United States Patent
Turbiez et al.

(10) Patent No.: US 11,217,752 B2
(45) Date of Patent: Jan. 4, 2022

(54) DIKETOPYRROLOPYRROLE POLYMERS AS ORGANIC SEMICONDUCTORS

(71) Applicant: BASF SE, Ludwigshafen (DE)

(72) Inventors: Mathieu G. R. Turbiez, Rixheim (FR); Rene Albert Johan Janssen, NS Heeze (NL); Martinus Maria Wienk, EC Tilburg (NL); Hans Juerg Kirner, Prattein (CH); Mathias Dueggeli, Basel (CH)

(73) Assignee: BASF SE, Ludwigshafen am Rhein (DE)

( * ) Notice: Subject to any disclaimer, the term of this patent is extended or adjusted under 35 U.S.C. 154(b) by 75 days.

(21) Appl. No.: 16/539,464

(22) Filed: Aug. 13, 2019

(65) Prior Publication Data

US 2019/0372007 A1 Dec. 5, 2019

Related U.S. Application Data

(63) Continuation of application No. 14/924,060, filed on Oct. 27, 2015, now Pat. No. 10,424,737, which is a (Continued)

(30) Foreign Application Priority Data

Jun. 30, 2006 (EP) .................. 06116391
Aug. 21, 2006 (EP) .................. 06119228

(51) Int. Cl.
*H01L 51/30* (2006.01)
*H01L 51/00* (2006.01)
(Continued)

(52) U.S. Cl.
CPC .......... *H01L 51/0036* (2013.01); *B82Y 10/00* (2013.01); *C07D 487/04* (2013.01);
(Continued)

(58) Field of Classification Search
CPC ............. H01L 51/0036; H01L 51/0043; H01L 51/0053; H01L 51/00; C08G 2261/3229
See application file for complete search history.

(56) References Cited

U.S. PATENT DOCUMENTS

| | | |
|---|---|---|
| 5,169,953 A | 12/1992 | Mizuguchi et al. |
| 5,484,943 A | 1/1996 | Zambounis et al. |

(Continued)

FOREIGN PATENT DOCUMENTS

| | | |
|---|---|---|
| EP | 0635539 | 1/1995 |
| EP | 1087005 | 3/2001 |

(Continued)

OTHER PUBLICATIONS

USPTO structure search, Mar. 2021.*
(Continued)

*Primary Examiner* — Gregory Listvoyb
(74) *Attorney, Agent, or Firm* — Armstrong Teasdale LLP

(57) ABSTRACT

A polymer includes repeating unit(s) of the formula (I). a, b, c, d, e and f are 0, 1, 2, or 3. $Ar^1$ and $Ar^{1'}$ are independently of each other a group of formula (AR1). $Ar^2$, $Ar^{2'}$, $Ar^3$, $Ar^{3'}$, $Ar^4$ and $Ar^{4'}$ are independently of each other a group of formula (AR2). The polymer is preferably a co-polymer.

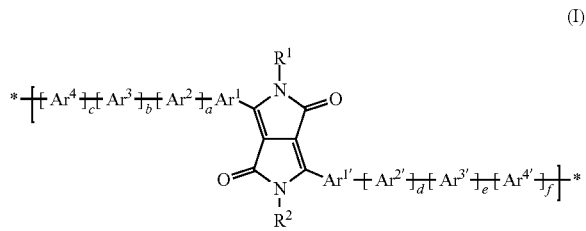

(I)

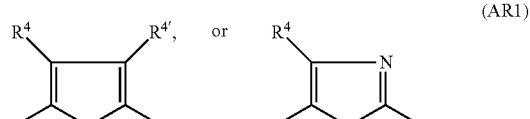

(AR1)

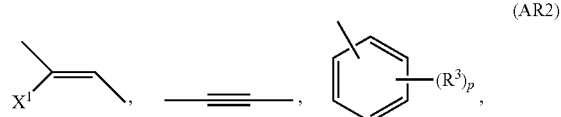

(AR2)

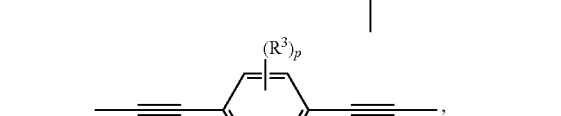

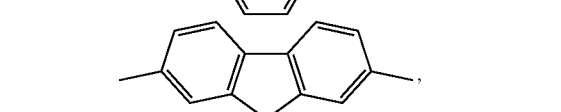

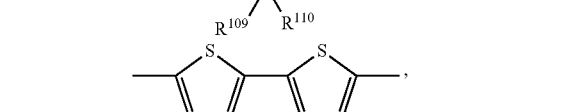

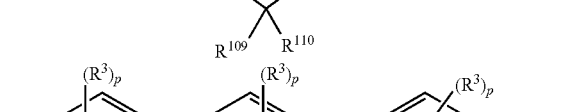

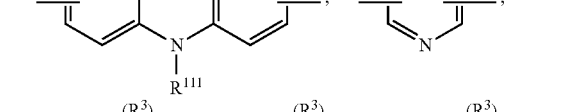

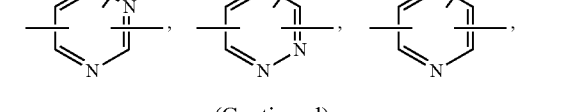

(Continued)

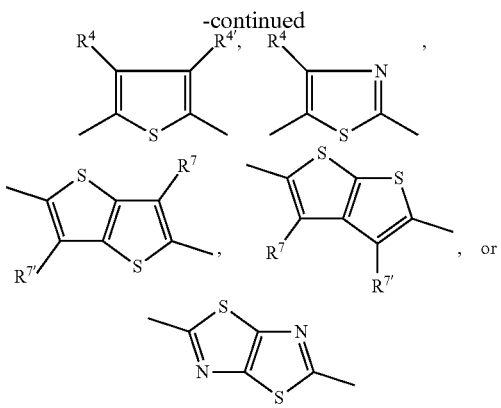

14 Claims, No Drawings

Related U.S. Application Data continuation of application No. 12/308,037, filed as application No. PCT/EP2007/056102 on Jun. 20, 2007, now abandoned.

(51) Int. Cl.

| | | |
|---|---|---|
| B82Y 10/00 | (2011.01) | |
| C07D 487/04 | (2006.01) | |
| C08G 61/00 | (2006.01) | |
| C08G 61/02 | (2006.01) | |
| C08G 61/12 | (2006.01) | |
| C09B 69/10 | (2006.01) | |
| H01L 51/05 | (2006.01) | |
| H01L 51/42 | (2006.01) | |
| H01L 51/50 | (2006.01) | |
| H01L 51/44 | (2006.01) | |

(52) U.S. Cl.
CPC ............ *C08G 61/00* (2013.01); *C08G 61/02* (2013.01); *C08G 61/122* (2013.01); *C08G 61/124* (2013.01); *C08G 61/126* (2013.01); *C09B 69/109* (2013.01); *H01L 51/0035* (2013.01); *H01L 51/0037* (2013.01); *H01L 51/0043* (2013.01); *H01L 51/0003* (2013.01); *H01L 51/0047* (2013.01); *H01L 51/0053* (2013.01); *H01L 51/0545* (2013.01); *H01L 51/0558* (2013.01); *H01L 51/4253* (2013.01); *H01L 51/44* (2013.01); *H01L 51/5012* (2013.01); *H01L 51/5088* (2013.01); *Y02E 10/549* (2013.01)

(56) References Cited

U.S. PATENT DOCUMENTS

| | | |
|---|---|---|
| 5,492,564 A | 2/1996 | Wooden et al. |
| 5,693,824 A | 12/1997 | Mizuguchi et al. |
| 5,708,188 A | 1/1998 | Hao et al. |
| 5,718,998 A | 2/1998 | Takahashi et al. |
| 5,750,723 A | 5/1998 | Eldin et al. |
| 6,388,093 B1 | 5/2002 | Chamberlain et al. |
| 6,451,459 B1 | 9/2002 | Tieke et al. |
| 7,910,684 B2 | 3/2011 | Li |
| 7,932,344 B2 | 4/2011 | Li |
| 7,939,818 B2* | 5/2011 | Heim ................... C08G 61/123 257/40 |
| 2003/0077541 A1 | 4/2003 | Shibuya et al. |
| 2004/0151944 A1 | 8/2004 | Onikubo et al. |
| 2005/0008892 A1 | 1/2005 | Yamamoto et al. |
| 2007/0010672 A1 | 1/2007 | Yamamoto et al. |
| 2007/0228359 A1 | 10/2007 | Heim et al. |
| 2009/0302311 A1 | 12/2009 | Turbiez et al. |
| 2011/0215313 A1 | 9/2011 | Dueggeli et al. |
| 2011/0240981 A1 | 10/2011 | Dueggeli et al. |
| 2012/0074393 A1 | 3/2012 | Wurthner et al. |

FOREIGN PATENT DOCUMENTS

| | | |
|---|---|---|
| EP | 1087006 | 3/2001 |
| EP | 1101800 | 5/2001 |
| EP | 2033983 | 3/2009 |
| EP | 2034537 | 3/2009 |
| JP | 2004/269698 | 9/2004 |
| JP | 2006-295004 | 10/2006 |
| WO | 98/25927 | 6/1998 |
| WO | 98/32802 | 7/1998 |
| WO | 2005/049695 | 6/2005 |
| WO | 2008/000664 | 1/2008 |
| WO | 2009/047104 | 4/2009 |
| WO | 2010/049321 | 5/2010 |
| WO | 2010/049323 | 5/2010 |
| WO | 2011/025454 | 3/2011 |

OTHER PUBLICATIONS

Beyerlein et al., Synthetic Metals, vol. 130, (2002), pp. 115-119.
Beyerlein et al., Macromol. Rapid Commun., vol. 21, (2000), pp. 182-189.
L. Bürgi, et al., "High-Mobility Ambipolar Near-Infrared Light-Emitting Polymer Field-Effect Transistors," *Adv. Mater.* vol. 20, 2008, pp. 2217-2224.
Smet et al., Tetrahedron Letters, vol. 42, (2001), pp. 6527-6530.
M. M. Wienk, et al., "Narrow-Bandgap Diketo-Pyrrolo-Pyrrole Polymer Solar Cells: The Effect of Processing on the Performance," *Adv. Mater*, vol. 20, 2008, pp. 2556-2560.
Patent Abstracts of Japan Publication No. 09003448, Jan. 7, 1997.
Lange et al., Macromol. Chem.. Phys., vol. 200, (1999), pp. 106-112.
Chan et al., J. Am Chem. Soc., vol. 115, (1993). pp. 11735-11743.
Bao et al., J. Am. Chem. Soc., vol. 117, (1995), p. 12426-12435.
Yu et al., Appl. Phys. Lett., vol. 64, No. 19, May 1994, pp. 2489-2491.
Zhu et al., Macromol. Chem. Phys., vol. 207, (2006), pp. 2206-2214.
English language abstract of EP 0635539, Jan. 25, 1995.
Yuning Li, et al., "A High Mobility P-Type DPP-Thieno[3,2-b]thiophene Copolymer for Organic Thin-Film Transistors", Advanced Material, 2010, 22, pp. 4862-4866.
Y. Zhu, et al., "Highly Luminescent 1,4-Diketo-3,6-diphenylpyrrolo[3,4-c]pyrrole-(DPP-) Based Conjugated Polymers Prepared Upon Suzuki Coupling", Macromolecules 2007, 40, pp. 6981-6989.
Derong Cao, et al., "Synthesis and Characterization of Novel Red-Emitting Alternating Copolymers Based on Fluorene and Diketopyrrolopyrrole Derivatives", Journal of Polymer Science: Part A: Polymer Chemistry 44 (2006) pp. 2395-2405.
A. R. Rabindranath, et al., "Red Emitting N-Functionalized Poly(1,4-diketo-3,6-diphenylpyrrolo[3,4-c]pyrrole) (Poly-DPP): A Deeply Colored Polymer with Unusually Large Stokes Shift", Macomolecules 39 (2006) pp. 8250-8256.

* cited by examiner

DIKETOPYRROLOPYRROLE POLYMERS AS ORGANIC SEMICONDUCTORS

CROSS-REFERENCE TO RELATED APPLICATIONS

The present application is a continuation application of U.S. patent application Ser. No. 14/924,060 filed Oct. 27, 2015, which in turn is a continuation application of U.S. patent application Ser. No. 12/308,037 filed Dec. 5, 2008, which in turn is a national stage of International Application No. PCT/EP2007/056102, filed Jun. 20, 2007, which claims priority to European Patent Application No. 06116391.1, filed Jun. 30, 2006 and to European Patent Application No. 06119228.2, filed Aug. 21, 2006. The contents of these applications are incorporated herein by reference in their entirety.

The present invention relates to polymers comprising a repeating unit of the formula (I) and their use as organic semiconductor in organic devices, especially a diode, an organic field effect transistor and/or a solar cell, or a device containing a diode and/or an organic field effect transistor, and/or a solar cell. The polymers according to the invention have excellent solubility in organic solvents and excellent film-forming properties. In addition, high efficiency of energy conversion, excellent field-effect mobility, good on/off current ratios and/or excellent stability can be observed, when the polymers according to the invention are used in semiconductor devices or organic photovoltaic (PV) devices (solar cells).

M. Smet et al., Tetrahedron Lett. 42 (2001) 6527-6530 describe the preparation of rod-like diketopyrrolopyrrole oligomers by a stepwise sequence of Suzuki couplings using brominated 1,4-dioxo-3,6-diphenylpyrrolo[3,4-c]pyrrole (DPP) derivatives and 1,4-dibromo-2,5-di-n-hexylbenzene as the monomers.

M. Horn et. al, Eur. Polymer J. 38 (2002) 2197-2205 decribe the synthesis and characterisation of thermomesogenic polysiloxanes with 2,5-dihydropyrrolo[3,4-c]pyrrole units in the main chain.

EP-A-787,730 describes a polyacrylate and a polyurethane obtained by the polymerization of a DPP of formula Ia

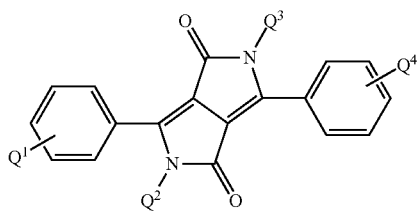

wherein $Q_1$ and $Q_4$ independently of each other stand for a polymerizable reactive group, and $Q_2$ and $Q_3$ independently of each other stand for hydrogen, $C_{12}$-$C_{24}$alkyl, $C_6$-$C_{24}$alkyl which is interrupted one or more times by O or S, or are a group of the formula

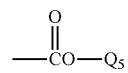

in which $Q_5$ is $C_4$-$C_{18}$alkyl or $C_5$-$C_{10}$cycloalkyl.

Though it is mentioned that compounds Ia can be used for the preparation of photo- and electroconductive polymers, no corresponding examples are given. Further, no teaching is given of how to prepare EL devices comprising DPP-based polymers and of how to select the appropriate DPP-monomers resp. DPP-polymers.

Macromol. Chem. Phys. 200 (1999) 106-112 describes fluorescent DPP-polymers obtainable by the copolymerization of bifunctional monomeric DPP-derivatives, wherein the functional groups are attached to the N-atoms of the DPP-molecule, with diisocyanates or di-ols or di-acids.

J. Am. Chem. Soc. 117 (1995) 12426-12435 relates to the exploration of the palladium catalysed Stille coupling reaction for the synthesis of functional polymers. In Scheme 7 the synthesis of the following polymers is presented:

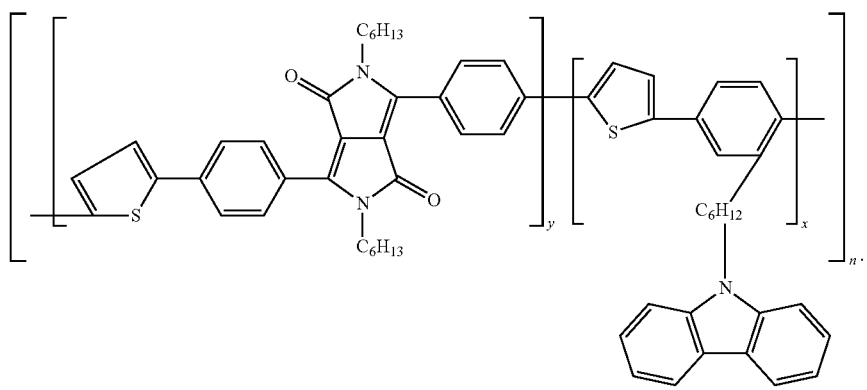

Polymer 13: y = 0,05, x = 0,95
Polymer 14: y = o, x = 1

No teaching is given whether the described polymers can be used in EL devices.

J. Am. Chem. Soc. 115 (1993) 11735-11743 describes DPP-polymers demonstrating photorefractivity, i.e. exhibiting photoconductivity and second order non-linear-optical activity. In this device, photoconductive properties are determined by irradiating the device with a laser beam and then measuring the current resulting from this irradiation, no measurements were carried out with regard to electroluminescence.

Further, no teaching is given of how to select other DPP-polymers.

In Appl. Phys. Lett. 64 (1994) 2489-2491 further studies, i.e. two-beam coupling experiments, using polymers disclosed in J. Am. Chem. Soc. 115 (1993) 11735-11743 are performed to study photorefractivity. The two-beam coupling experiments demonstrated asymmetric energy exchange under zero field, i.e. photorefractivity of the polymers disclosed in J. Am. Chem. Soc. 115 (1993) 11735-11743.

U.S. Pat. No. 6,451,459B (cf. B. Tieke et al., Synth. Met. 130 (2002) 115-119; Macromol. Rapid Commun. 21 (4) (2000) 182-189) describes diketopyrrolopyrrole based polymers and copolymers comprising the following units

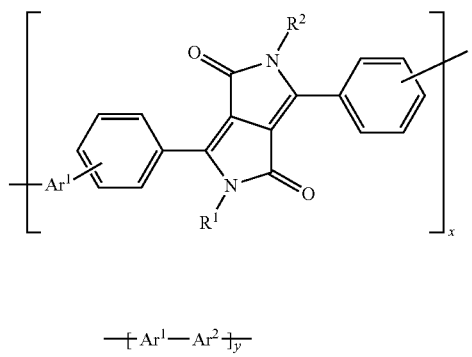

wherein x is chosen in the range of from 0.005 to 1, preferably from 0.01 to 1, and y from 0.995 to 0, preferably 0.99 to 0, and wherein x+y=1, and wherein $Ar^1$ and $Ar^2$ independently from each other stand for

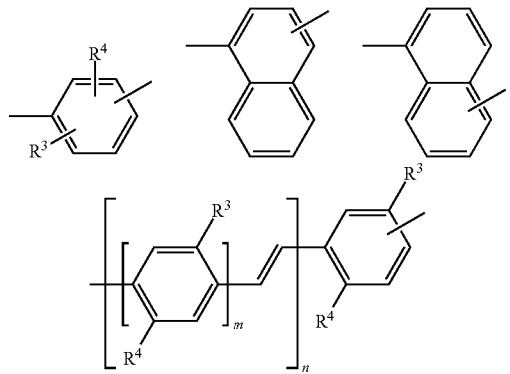

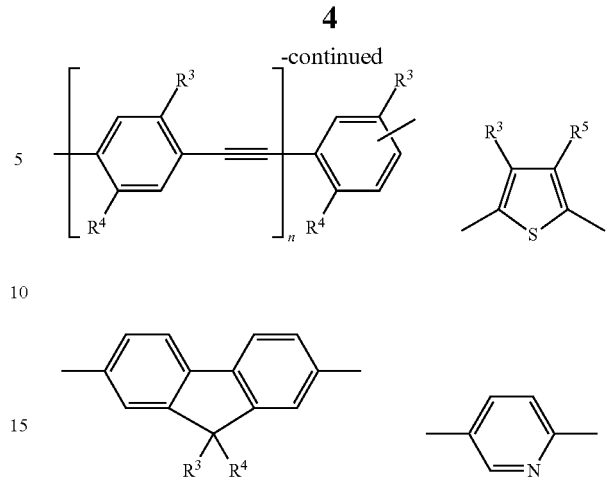

and m, n being numbers from 1 to 10, and $R^1$ and $R^2$ independently from each other stand for H, $C_1$-$C_{18}$alkyl, —C(O)O—$C_1$-$C_{18}$alkyl, perfluoro-$C_1$-$C_{12}$alkyl, unsubstituted $C_6$-$C_{12}$aryl or one to three times with $C_1$-$C_{12}$alkyl, $C_1$-$C_{12}$alkoxy, or halogen substituted $C_6$-$C_{12}$aryl, $C_1$-$C_{12}$alkyl-$C_6$-$C_{12}$aryl, or $C_6$-$C_{12}$aryl-$C_1$-$C_{12}$alkyl, $R^3$ and $R^4$ preferably stand for hydrogen, $C_1$-$C_{12}$alkyl, $C_1$-$C_{12}$alkoxy, unsubstituted $C_6$-$C_{12}$aryl or one to three times with $C_1$-$C_{12}$alkyl, $C_1$-$C_{12}$alkoxy, or halogen substituted $C_6$-$C_{12}$aryl or perfluoro-$C_1$-$C_{12}$alkyl, and $R^5$ preferably stands for $C_1$-$C_{12}$alkyl, $C_1$-$C_{12}$alkoxy, unsubstituted $C_6$-$C_{12}$aryl or one to three times with $C_1$-$C_{12}$alkyl, $C_1$-$C_{12}$alkoxy, or halogen substituted $C_6$-$C_{12}$aryl, or perfluoro-$C_1$-$C_{12}$alkyl, and their use in EL devices. The following polymer

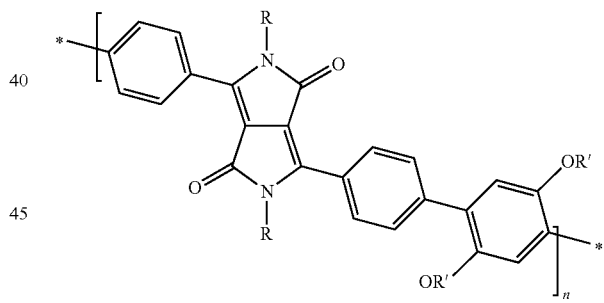

is explicitly disclosed in Tieke et al., Synth. Met. 130 (2002) 115-119. The following polymers

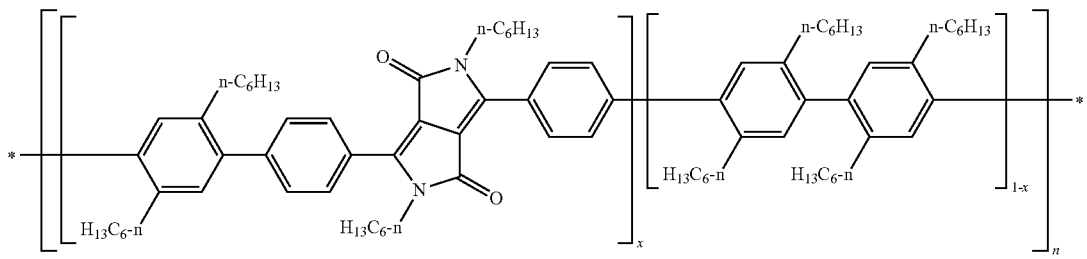

are explicitly disclosed in Macromol. Rapid Commun. 21 (4) (2000) 182-189.

WO05/049695 discloses diketopyrrolopyrrole (DPP) based polymers and their use in PLEDs, organic integrated circuits (O-ICs), organic field effect transistors (OFETs), organic thin film transistors (OTFTs), organic solar cells (O-SCs), or organic laser diodes, but fails to disclose the specific DPP based polymers of formula I. In Example 12 the preparation of the following polymer is described:

The object of the present invention is to provide novel polymers which show excellent performance when used, for example, in semiconductor devices, photodiodes or organic photovoltaic (PV) devices (solar cells), such as high efficiency of energy conversion, excellent field-effect mobility, good on/off current ratios and/or excellent stability.

Said object is achieved by polymers comprising repeating units of the formula

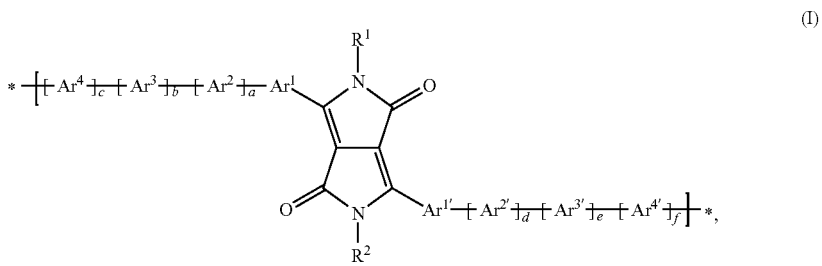

(I), wherein a, b, c, d, e and f are 0 to 200, especially 0, 1, 2, or 3;

$Ar^1$ and $Ar^{1'}$ are independently of each other a group of formula

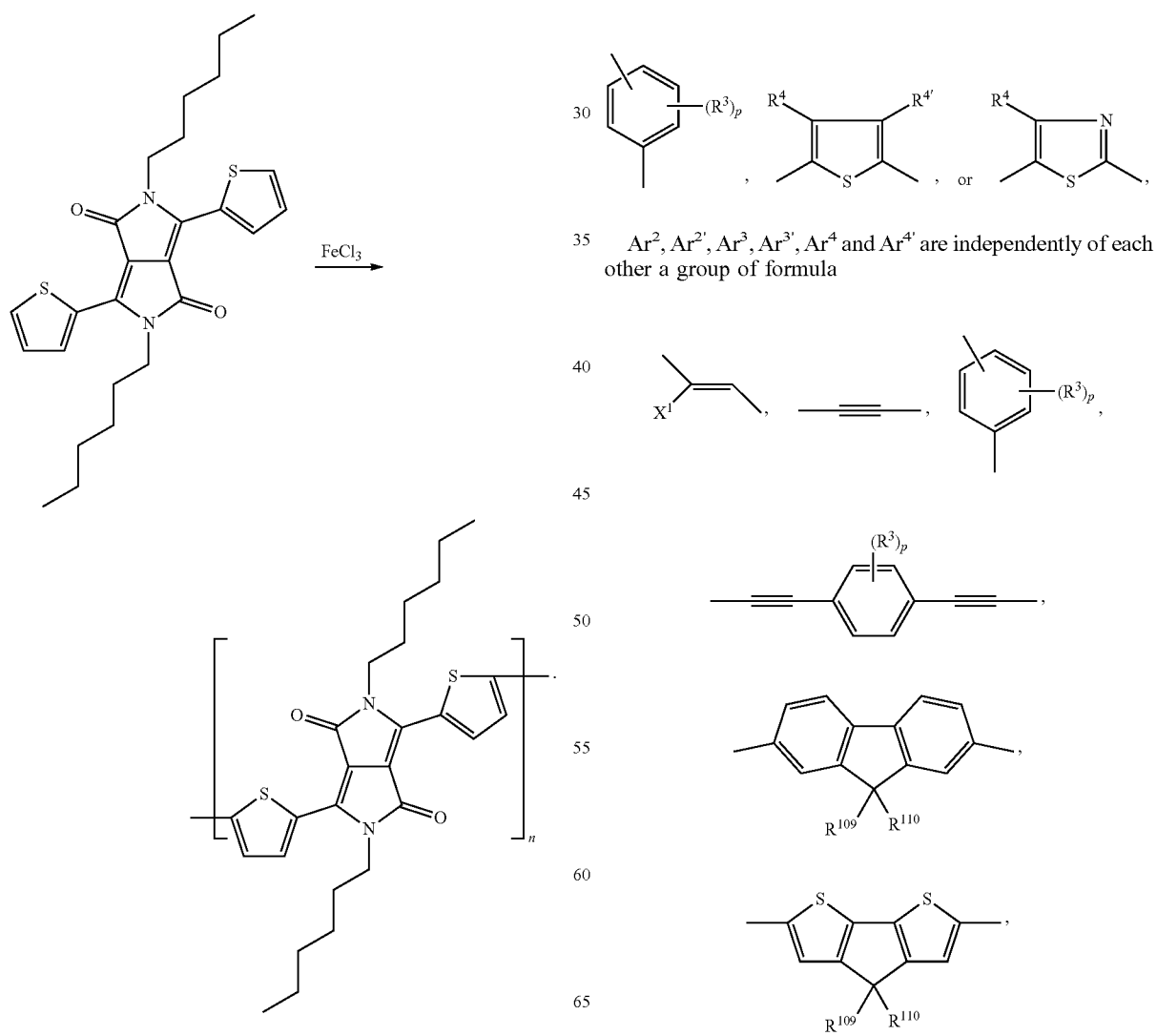

$Ar^2$, $Ar^{2'}$, $Ar^3$, $Ar^{3'}$, $Ar^4$ and $Ar^{4'}$ are independently of each other a group of formula

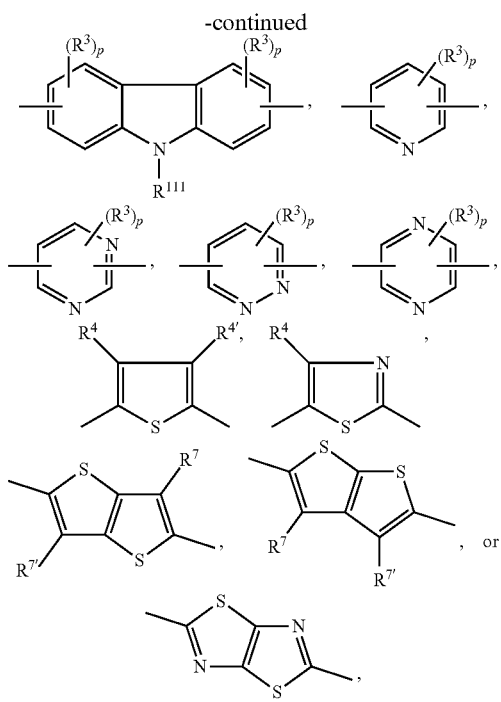

p stands for 0, 1, 2, 3 or 4, if possible, $R^1$ and $R^2$ may be the same or different and are selected from hydrogen, a $C_1$-$C_{25}$alkyl group, an alkenyl group, an alkynyl group, which may optionally be substituted by E and/or interrupted by D, an allyl group, which can be substituted one to three times with $C_1$-$C_4$alkyl; a cycloalkyl group, which can be substituted one to three times with $C_1$-$C_8$alkyl, $C_1$-$C_8$thioalkoxy, or $C_1$-$C_8$alkoxy, or a cycloalkyl group, which can be condensed one or two times by phenyl, which can be substituted one to three times with $C_1$-$C_4$-alkyl, halogen, nitro or cyano; a cycloalkenyl group, a ketone or aldehyde group, an ester group, a carbamoyl group, a silyl group, a siloxanyl group, $Ar^{10}$ or —$CR^5R^6$—$(CH_2)_g$—$Ar^{10}$, wherein $R^5$ and $R^6$ independently from each other stand for hydrogen, fluorine, cyano or $C_1$-$C_4$alkyl, which can be substituted by fluorine, chlorine or bromine, or phenyl, which can be substituted one to three times with $C_1$-$C_4$alkyl, $Ar^{10}$ stands for aryl or heteroaryl, which may optionally be substituted by G, in particular phenyl or 1- or 2-naphthyl which can be substituted one to three times with $C_1$-$C_8$alkyl, $C_1$-$C_8$thioalkoxy, and/or $C_1$-$C_8$alkoxy, and g stands for 0, 1, 2, 3 or 4, $R^3$ may be the same or different within one group and is selected from $C_1$-$C_{25}$alkyl, which may optionally be substituted by E and/or interrupted by D, $C_6$-$C_{24}$aryl, which may optionally be substituted by G, $C_2$-$C_{20}$heteroaryl, which may optionally be substituted by G, $C_1$-$C_{18}$alkoxy, which may optionally be substituted by E and/or interrupted by D, $C_7$-$C_{28}$aralkyl, wherein ar (=aryl) of aralkyl may optionally be substituted by G, or —CO—$R^{26}$, or two or more groups $R^3$ which are in the neighbourhood to each other, form a ring;

$R^4$, $R^{4'}$, $R^7$ and $R^{7'}$ independently from each other stand for hydrogen, $C_1$-$C_{25}$alkyl, which may optionally be substituted by E and/or interrupted by D, $C_6$-$C_{24}$aryl, which may optionally be substituted by G, $C_2$-$C_{20}$heteroaryl, which may optionally be substituted by G, $C_1$-$C_{18}$alkoxy, which may optionally be substituted by E and/or interrupted by D, $C_7$-$C_{25}$aralkyl, wherein ar (=aryl) of aralkyl may optionally be substituted by G, or —CO—$R^{28}$; or $R^4$ and $R^{4'}$ form a ring;

D is —CO—; —COO—; —S—; —SO—; —SO$_2$—; —NR$^{25}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; or halogen; G is E, $C_1$-$C_{18}$alkyl, which may be interrupted by D, or $C_1$-$C_{18}$alkoxy which is substituted by E and/or interrupted by D, wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{27}$ and $R^{28}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is H; $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{109}$ and $R^{110}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{109}$ and $R^{110}$ together form a group of formula =$CR^{100}R^{101}$, wherein $R^{100}$ and $R^{101}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{109}$ and $R^{110}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{18}$, $R^{111}$ is H, a $C_1$-$C_{25}$alkyl group, a $C_4$-$C_{18}$cycloalkyl group, a $C_1$-$C_{25}$alkoxy group, in which one or more carbon atoms which are not in neighbourhood to each other could be replaced by —O—, —S—, or —C(=O)—O—, and/or wherein one or more hydrogen atoms can be replaced by F, a $C_6$-$C_{24}$aryl group, or a $C_6$-$C_{24}$aryloxy group, wherein one or more carbon atoms can be replaced by O, S, or N, and/or which can be substituted by one or more non-aromatic groups $R^{111}$;

m can be the same or different at each occurrence and is 0, 1, 2, or 3, especially 0, 1, or 2, very especially 0 or 1;

$X^1$ is a hydrogen atom, or a cyano group, with the proviso that, if $Ar^1$ and $Ar^{1'}$ are a group of formula

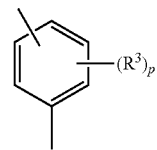

and a and d are both 1 and $Ar^2$ and $Ar^{2'}$ are different from a group of formula

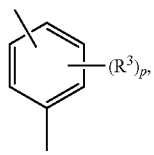

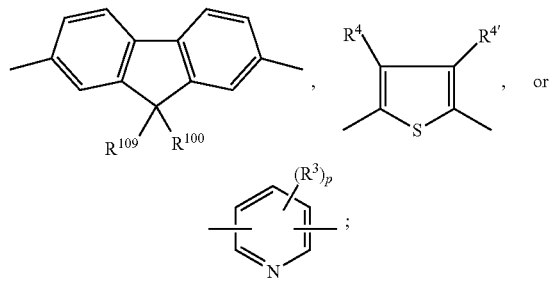

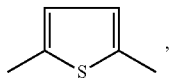

with the proviso that, if $Ar^1$ and $Ar^{1'}$ are a group of formula

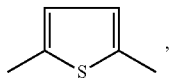

a and d are not 0;
and with the proviso, that a polymer of the formula

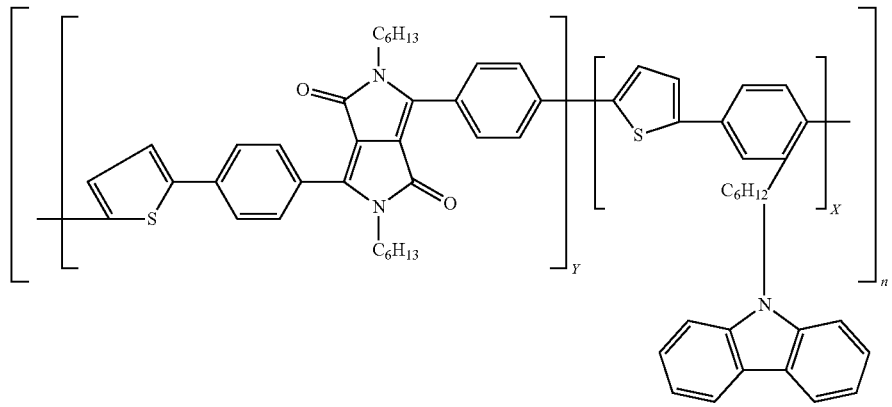

y = 0.05, x = 0.95 is excluded.

The polymers, wherein $R^1$ and/or $R^2$ are hydrogen can be obtained by using a protecting group which can be removed after polymerization (see, for example, EP-A-0 648 770, EP-A-0 648 817, EP-A-0 742 255, EP-A-0 761 772, WO98/32802, WO98/45757, WO98/58027, WO99/01511, WO00/17275, WO00/39221, WO00/63297 and EP-A-1 086 984). Conversion of the pigment precursor into its pigmentary form is carried out by means of fragmentation under known conditions, for example thermally, optionally in the presence of an additional catalyst, for example the catalysts described in WO00/36210.

An example of such a protecting group is group of formula

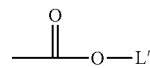

wherein L is any desired group suitable for imparting solubility.

L is preferably a group of formula

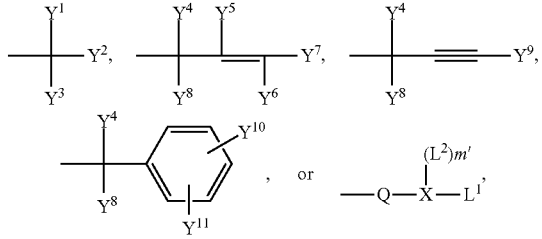

wherein $Y^1$, $Y^2$ and $Y^3$ are independently of each other $C_1$-$C_6$alkyl, $Y^4$ and $Y^8$ are independently of each other $C_1$-$C_6$alkyl, $C_1$-$C_6$alkyl interrupted by oxygen, sulfur or $N(Y^{12})_2$, or unsubstituted or $C_1$-$C_6$alkyl-, $C_1$-$C_6$alkoxy-, halo-, cyano- or nitro-substituted phenyl or biphenyl, $Y^5$, $Y^6$ and $Y^7$ are independently of each other hydrogen or $C_1$-$C_6$alkyl, $Y^9$ is hydrogen, $C_1$-$C_6$alkyl or a group of formula

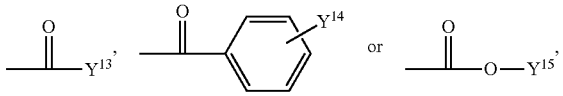

$Y^{10}$ and $Y^{11}$ are each independently of the other hydrogen, $C_1$-$C_6$alkyl, $C_1$-$C_6$alkoxy, halogen, cyano, nitro, $N(Y^{12})_2$, or unsubstituted or halo-, cyano-, nitro-, $C_1$-$C_6$alkyl- or $C_1$-$C_6$alkoxy-substituted phenyl, $Y^{12}$ and $Y^{13}$ are $C_1$-$C_6$alkyl, $Y^{14}$ is hydrogen or $C_1$-$C_6$alkyl, and $Y^{15}$ is hydrogen, $C_1$-$C_6$alkyl, or unsubstituted or $C_1$-$C_6$alkyl-substituted phenyl, Q is p,q-$C_2$-$C_6$alkylene unsubstituted or mono- or poly-substituted by $C_1$-$C_6$alkoxy, $C_1$-$C_6$alkylthio or $C_2$-$C_{12}$dialkylamino, wherein p and q are different position numbers, X is a hetero atom selected from the group consisting of nitrogen, oxygen and sulfur, m being the number 0 when X is oxygen or sulfur and m being the number 1 when X is nitrogen, and $L^1$ and $L^2$ are independently of each other unsubstituted or mono- or poly-$C_1$-$C_{12}$alkoxy-, —$C_1$-$C_{12}$alkylthio-, —$C_2$-$C_{24}$dialkylamino-, —$C_6$-$C_{12}$aryloxy-, —$C_6$-$C_{12}$arylthio-, —$C_7$-$C_{24}$alkylarylamino- or —$C_{12}$-$C_{24}$diarylamino-substituted $C_1$-$C_6$alkyl or [-(p',q'-$C_2$-$C_6$alkylene)-Z-]$_n$-$C_1$-$C_6$alkyl, n' being a number from 1 to 1000, p' and q' being different position numbers, each Z independently of any others being a hetero atom oxygen, sulfur or $C_1$-$C_{12}$alkyl-substituted nitrogen, and it being possible for $C_2$-$C_6$alkylene in the repeating [—$C_2$-$C_6$alkylene-Z-] units to be the same or different, and $L_1$ and $L_2$ may be saturated or unsaturated from one to ten times, may be uninterrupted or interrupted at any location by from 1 to 10 groups selected from the group consisting of —(C=O)— and —$C_6H_4$—, and may carry no further substituents or from 1 to 10 further substituents selected from the group consisting of halogen, cyano and nitro. Most preferred L is a group of formula

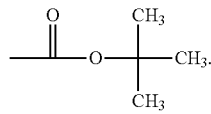

The polymers of the present invention can be used as charge-transport, semiconducting, el. conducting, photoconducting, light emitting material, surface-modifying material, electrode materials in batteries, alignment layers, or in OFETs, ICs, TFTs, displays, RFITD tags, electro- or photoluminescent devices, backlights of displays, photovoltaic or sensor devices, charge injection layers, Schottky diodes, memory devices (e.g. FeFET), planarising layers, antistatics, conductive substrates or patterns, photoconductors, or electrophotographic applications (recording).

The polymers of the present invention can comprise one, or more (different) repeating units of formula I, such as, for example, repeating units of formula Ia and Id.

The repeating unit of formula I can have an asymmetric structure, but has preferably a symmetric structure: a=d; b=e; c=f; $Ar^1$=$Ar^{1'}$; $Ar^2$=$Ar^{2'}$; $Ar^3$=$Ar^{3'}$; $Ar^4$=$Ar^{4'}$.

$R^1$ and $R^2$ may be the same or different and are preferably selected from hydrogen, a $C_1$-$C_{25}$alkyl group, which can optionally be interrupted by one or more oxygen atoms, a $C_1$-$C_{25}$perfluoroalkyl group, an allyl group, which can be substituted one to three times with $C_1$-$C_4$alkyl; a cycloalkyl group, which can be substituted one to three times with $C_1$-$C_8$alkyl, $C_1$-$C_8$thioalkoxy, or $C_1$-$C_8$alkoxy, or a cycloalkyl group, which can be condensed one or two times by phenyl, which can be substituted one to three times with $C_1$-$C_4$-alkyl, halogen, nitro or cyano, an alkenyl group, a cycloalkenyl group, an alkynyl group, a haloalkyl group, a haloalkenyl group, a haloalkynyl group, a ketone or aldehyde group, an ester group, a carbamoyl group, a ketone group, a silyl group, a siloxanyl group, $Ar^{10}$ or —$CR^5R^6$—$(CH_2)_g$—$Ar^{10}$, wherein $R^5$ and $R^6$ independently from each other stand for hydrogen, fluorine, cyano or $C_1$-$C_4$alkyl, which can be substituted by fluorine, chlorine or bromine, or phenyl, which can be substituted one to three times with $C_1$-$C_4$alkyl, $R^1$ and $R^2$ are more preferably selected from $C_1$-$C_{25}$alkyl, which can optionally be interrupted by one or more oxygen atoms, $C_5$-$C_{12}$-cycloalkyl, especially cyclohexyl, which can be substituted one to three times with $C_1$-$C_8$alkyl and/or $C_1$-$C_8$alkoxy, or $C_5$-$C_{12}$cycloalkyl, especially cyclohexyl, which can be condensed one or two times by phenyl, which can be substituted one to three times with $C_1$-$C_4$alkyl, halogen, nitro or cyano, phenyl or 1- or 2-naphthyl which can be substituted one to three times with $C_1$-$C_8$alkyl and/or $C_1$-$C_8$alkoxy, or —$CR^5R^6$—$(CH_2)_g$—$Ar^{10}$ wherein $R^3$ and $R^4$ stand for hydrogen, $Ar^{10}$ stands for phenyl or 1- or 2-naphthyl, which can be substituted one to three times with $C_1$-$C_8$alkyl and/or $C_1$-$C_8$alkoxy, and g stands for 0 or 1. An alkyl group which is interrupted one or more times by —O— is understood to be a straight-chain or branched $C_2$-$C_{25}$alkyl radical, which may be interrupted one or more times by —O—, for example one, two or three times by —O—, resulting in structural units such as, for example, —$(CH_2)_2OCH_3$, —$(CH_2CH_2O)_2CH_2CH_3$, —$CH_2$—O—$CH_3$, —$CH_2CH_2$—O—$CH_2CH_3$, —$CH_2CH_2CH_2$—O—$CH(CH_3)_2$, —$[CH_2CH_2O]_{Y1}$—$CH_3$ wherein Y1=1–10, —$CH_2$—$CH(CH_3)$—O—$CH_2$—$CH_2CH_3$ and —$CH_2$—$CH(CH_3)$—O—$CH_2$—$CH_3$.

Most preferred $R^1$ and $R^2$ are a $C_1$-$C_{25}$alkyl group, especially a $C_4$-$C_{25}$alkyl group, such as n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethyl-butyl and 2-ethylhexyl, n-nonyl, n-decyl, n-undecyl, n-dodecyl, tridecyl, tetradecyl, pentadecyl, hexadecyl, 2-hexyldecyl, heptadecyl, octadecyl, eicosyl, heneicosyl, docosyl, tetracosyl or pentacosyl, wherein advantageous groups can be represented by formula

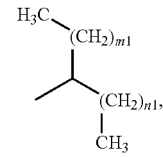

wherein m1=n1+4 and m1+n1≤22.

Chiral side chains, such as $R^1$ and $R^2$, can either be homochiral, or racemic, which can influence the morphology of the polymers.

The present invention does not comprise polymers of formula I, wherein $R^1$ and $R^2$ are independently of each other a $C_1$-$C_{25}$alkyl group, especially a $C_4$-$C_{12}$alkyl group, which can be interrupted by one or more oxygen atoms, $Ar^1$ and $Ar^{1'}$ are a group of formula

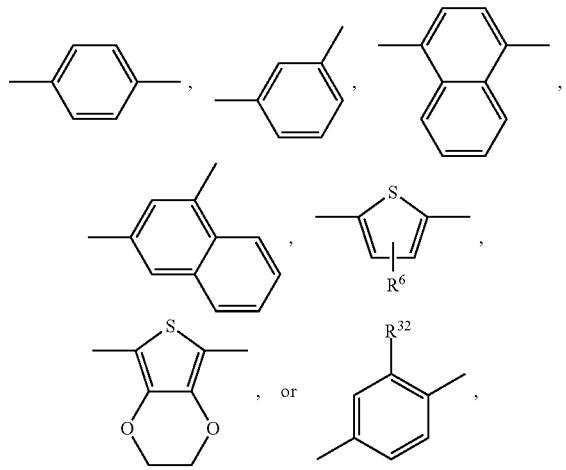

wherein R⁶ is hydrogen, $C_1$-$C_{18}$alkyl, or $C_1$-$C_{18}$alkoxy, and R³² is methyl, Cl, or OMe,
a=b=c=f=0; d=e=1;
Ar²' is selected from

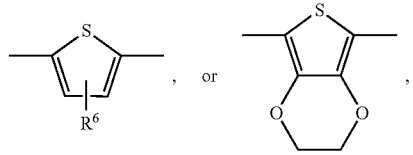

wherein
R⁶ is hydrogen, $C_1$-$C_{18}$alkyl, or $C_1$-$C_{18}$alkoxy, and
Ar³' is selected from

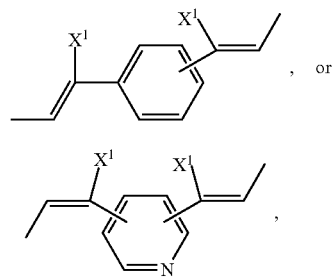
(VIb)

wherein
X¹ is a hydrogen atom, or a cyano group.
Ar¹ and Ar¹' can be different, but are preferably the same and are a group of formula

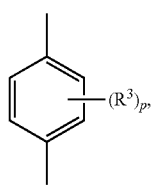

especially

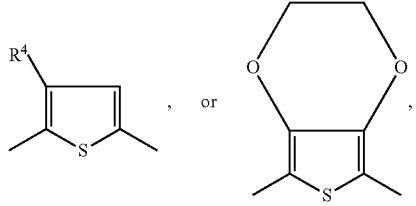

and Ar², Ar²', Ar³, Ar³', Ar⁴ and Ar⁴' are independently of each other a group of formula

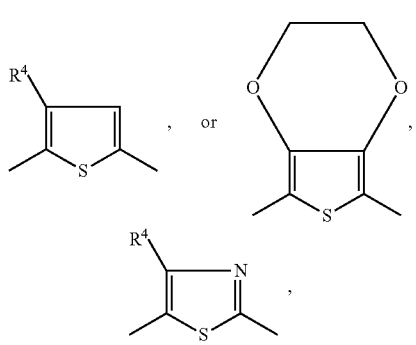

wherein
p stands for 0, 1, or 2, R³ may be the same or different within one group and is selected from $C_1$-$C_{25}$alkyl, which may optionally be substituted by E and/or interrupted by D, or $C_1$-$C_{18}$alkoxy, which may optionally be substituted by E and/or interrupted by D; R⁴ is $C_6$-$C_{25}$alkyl, which may optionally be substituted by E and/or interrupted by D, $C_6$-$C_{14}$aryl, such as phenyl, naphthyl, or biphenylyl, which may optionally be substituted by G, $C_1$-$C_{25}$alkoxy, which may optionally be substituted by E and/or interrupted by D, or $C_7$-$C_{15}$aralkyl, wherein ar may optionally be substituted by G, D is —CO—, —COO—, —S—, —SO—, —SO₂—, —O—, —NR²⁵—, wherein R²⁵ is $C_1$-$C_{12}$alkyl, such as methyl, ethyl, n-propyl, iso-propyl, n-butyl, isobutyl, or sec-butyl;

E is —OR²⁹; —SR²⁹; —NR²⁵R²⁵; —COR²⁸; —COOR²⁷; —CONR²⁵R²⁵; or —CN; wherein R²⁵, R²⁷, R²⁸ and R²⁹ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$ aryl, such as phenyl, naphthyl, or biphenylyl, G has the same preferences as E, or is $C_1$-$C_{18}$alkyl, especially $C_1$-$C_{12}$alkyl, such as methyl, ethyl, n-propyl, iso-propyl, n-butyl, isobutyl, sec-butyl, hexyl, octyl, or 2-ethyl-hexyl.

The units

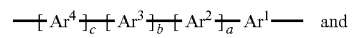
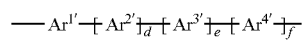

may be different, but are preferably the same and are a group of formula

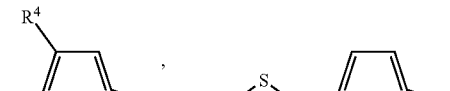
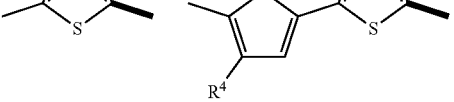
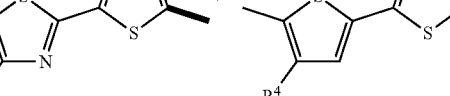
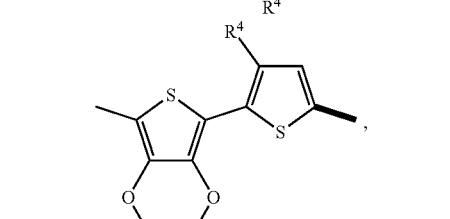
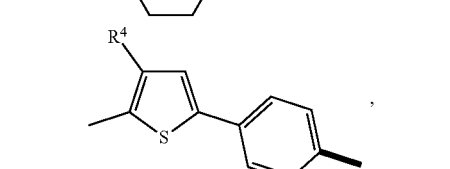

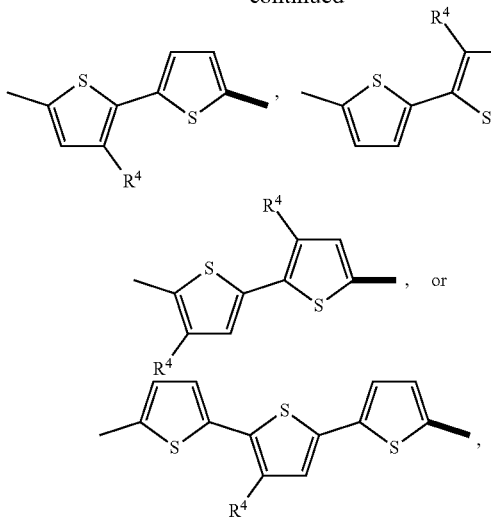

wherein ▬ indicates the bond to the diketopyrrolopyrrole skeleton, and $R^4$ is as defined above and $R^4$ has the meaning of $R^4$.

In another preferred embodiment of the present invention the units

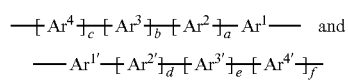

may be different, but are preferably the same and are a group of formula

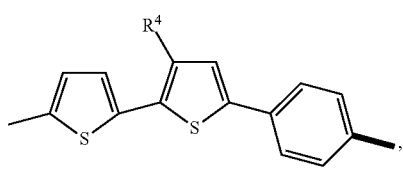

wherein $R^4$ is $C_6$-$C_{25}$alkyl, which may optionally be interrupted by one or more oxygen atoms.

In another preferred embodiment of the present invention the polymer comprises repeating units of the formula

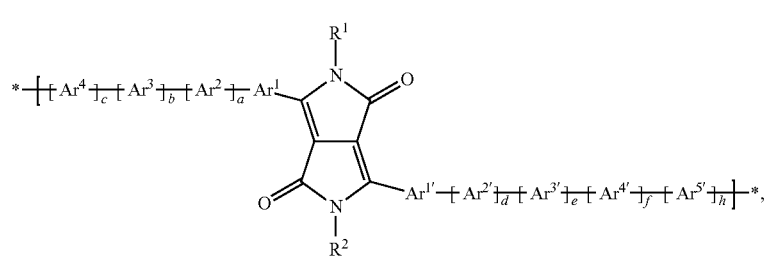

wherein a, b, c, d, e, f, $R^1$, $R^2$, $Ar^1$, $Ar^{1'}$, $Ar^2$, $Ar^{2'}$, $Ar^3$, $Ar^{3'}$, $Ar^4$ and $Ar^{4'}$ are as defined above, h is 1, and $Ar^5$ is a group of formula

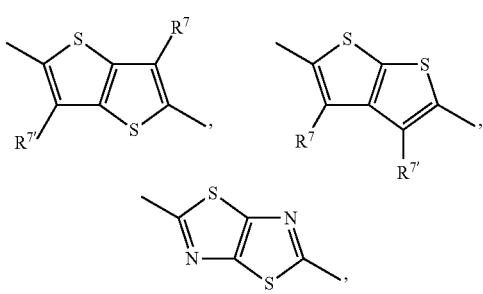

wherein $R^7$ and $R^{7'}$ are as defined above; or the polymer has the structure of formula $$*\text{—}[\text{First Repeating Unit}]_q\text{—}[\text{Branching Unit}]_t\text{—}*, \quad (III)$$

wherein the First "Repeating Unit" is a repeating unit of formula I, the "Branching Unit" is a unit having more than two linkage sites, and q and t are integers, wherein q/t is the ratio of the repeating unit of formula I to the "Branching Unit".

The repeating unit of formula II has advantageously a symmetric structure: a=d; b=e; c=f; $Ar^1$=$Ar^{1'}$; $Ar^2$=$Ar^{2'}$; $Ar^3$=$Ar^{3'}$; $Ar^4$=$Ar^{4'}$.

The "Branching Unit" is a unit having more than two linkage sites. Examples of branching units are, for example, described in Dendrimers and Other Dendritic Polymers, D. A. Tomalia, J. M. J. Fréchet (Eds), John Wiley & Sons, Ltd. 2002; Star and Hyperbranched Polymers, M. K. Mishra and S. Kobayashi (Eds), Marcel Dekker 2000.

Examples of especially suitable "Branching" Units are shown below:

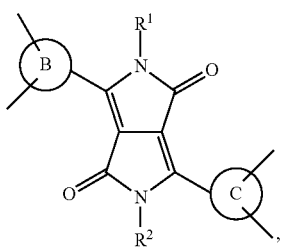

wherein B and C are independently of each other an optionally condensed aromatic, or heteroaromatic ring, such as

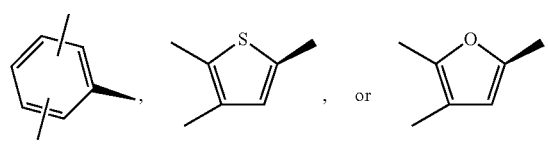
◀ is the bonding to the DPP backbone, especially
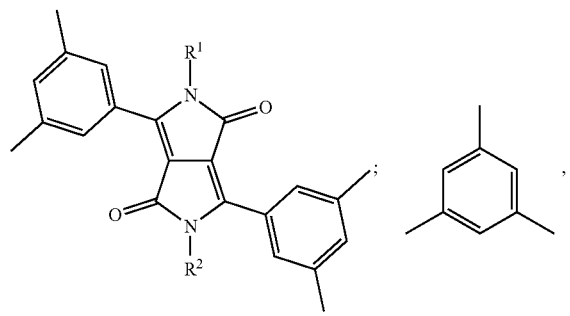
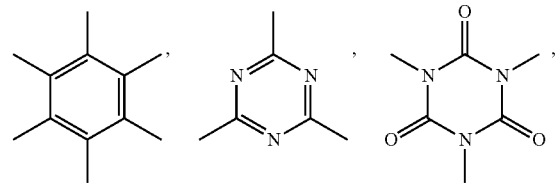
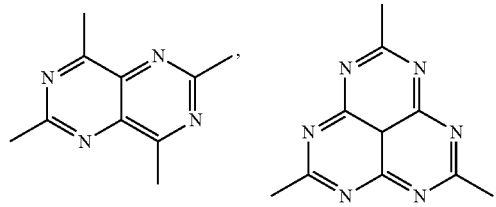
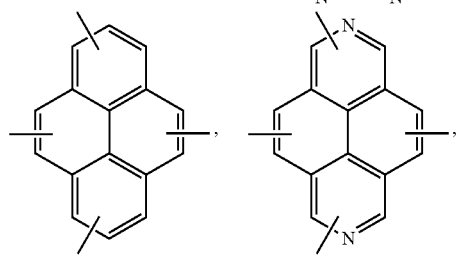
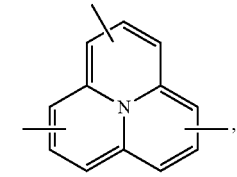
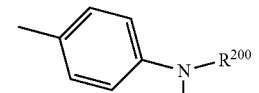
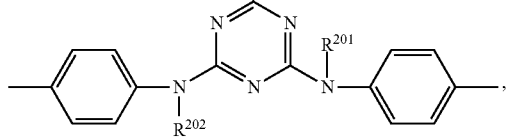
wherein $R^{200}$, $R^{201}$ and $R^{202}$ are independently of each other H, or $C_1$-$C_{25}$alkyl,
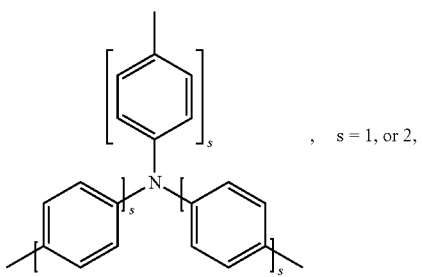
, s = 1, or 2,
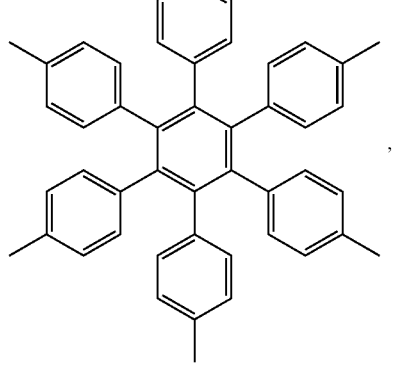
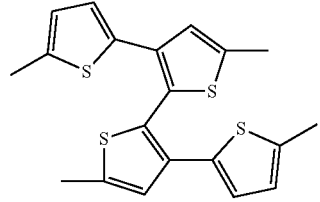
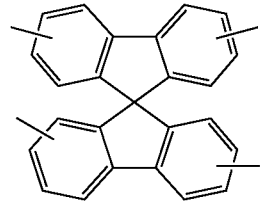
, such as
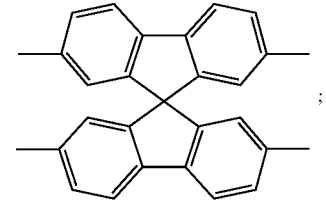
;
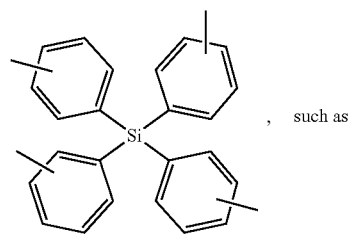
, such as

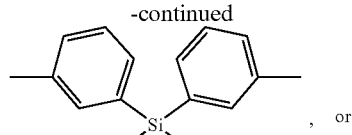, or
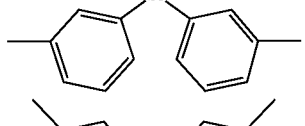; or
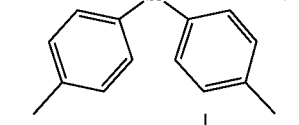, such as
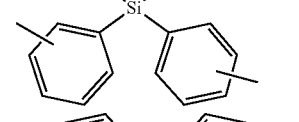, or
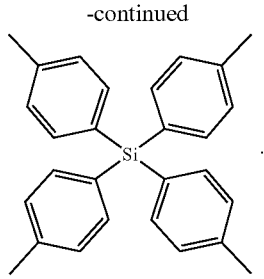.
The use of a multi-functional unit ("Branching Unit") results in branched polymeric materials, as illustrated below (for exemplary purposes only) for two multi-functional units:
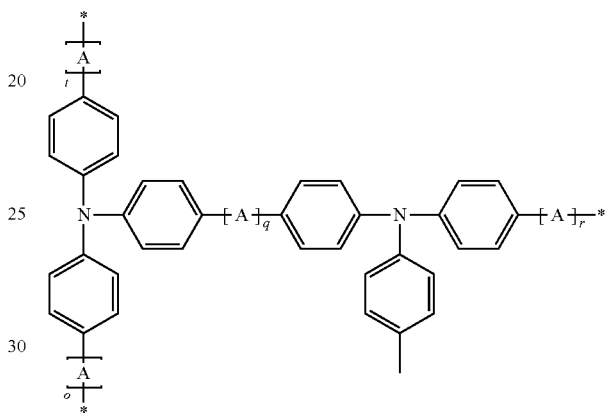
(A is a repeating unit of formula I, o, q, r and t are 0 to 500), or
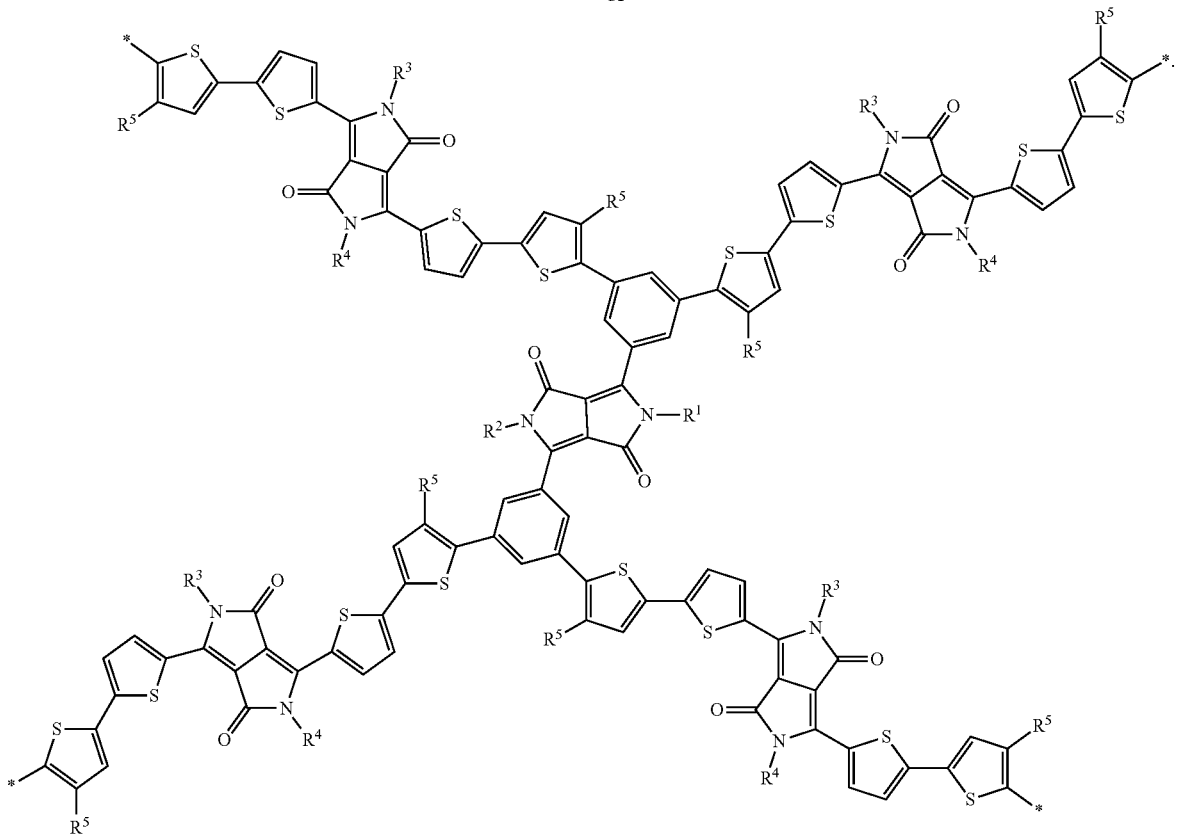

The "Branching Unit" of formula
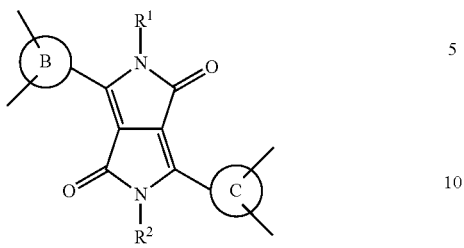
5
10
and polymers derived there from are new and form further aspects of the present invention.
In another preferred embodiment of the present invention the polymers comprise repeating units of the formula
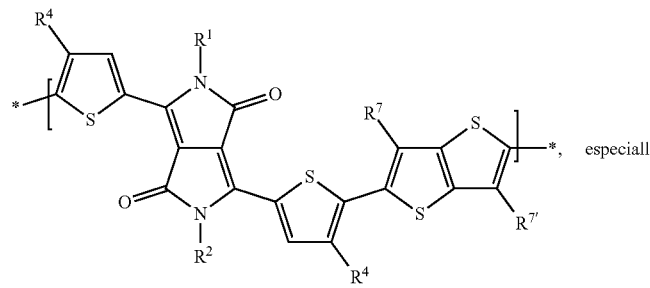, especially
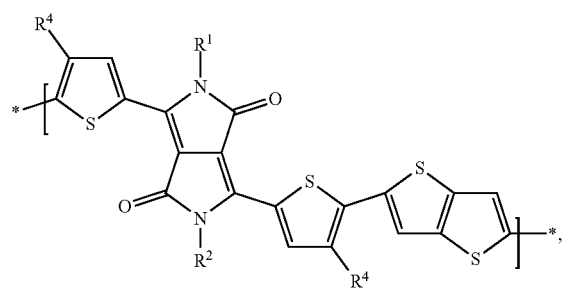,
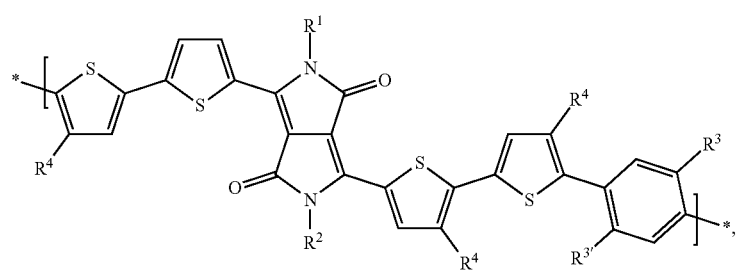,
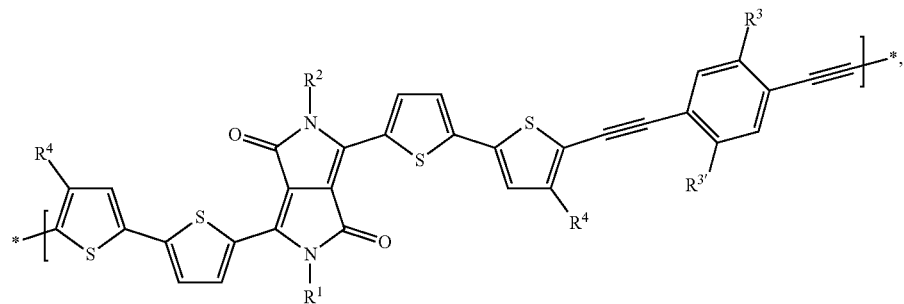, -continued
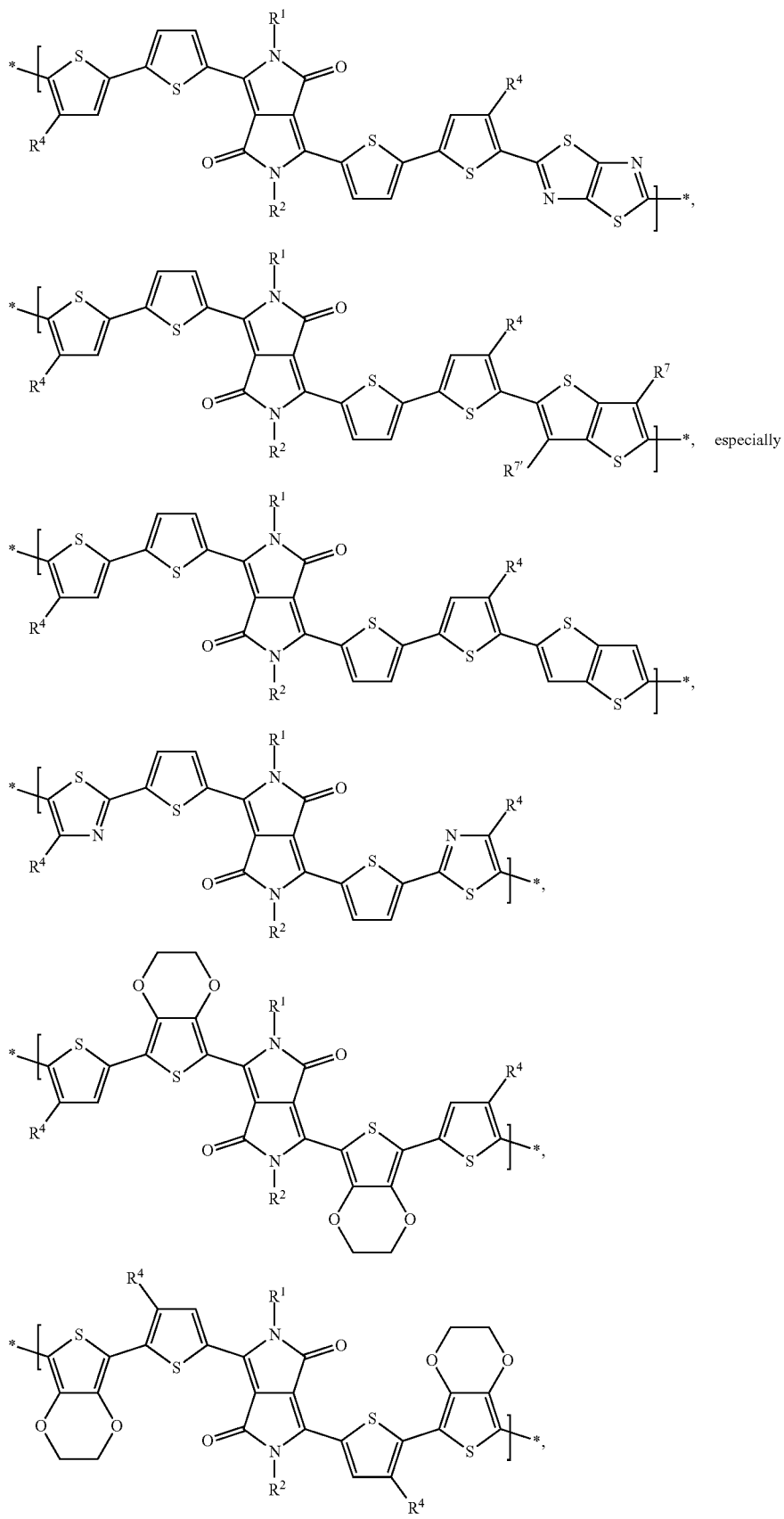
, especially

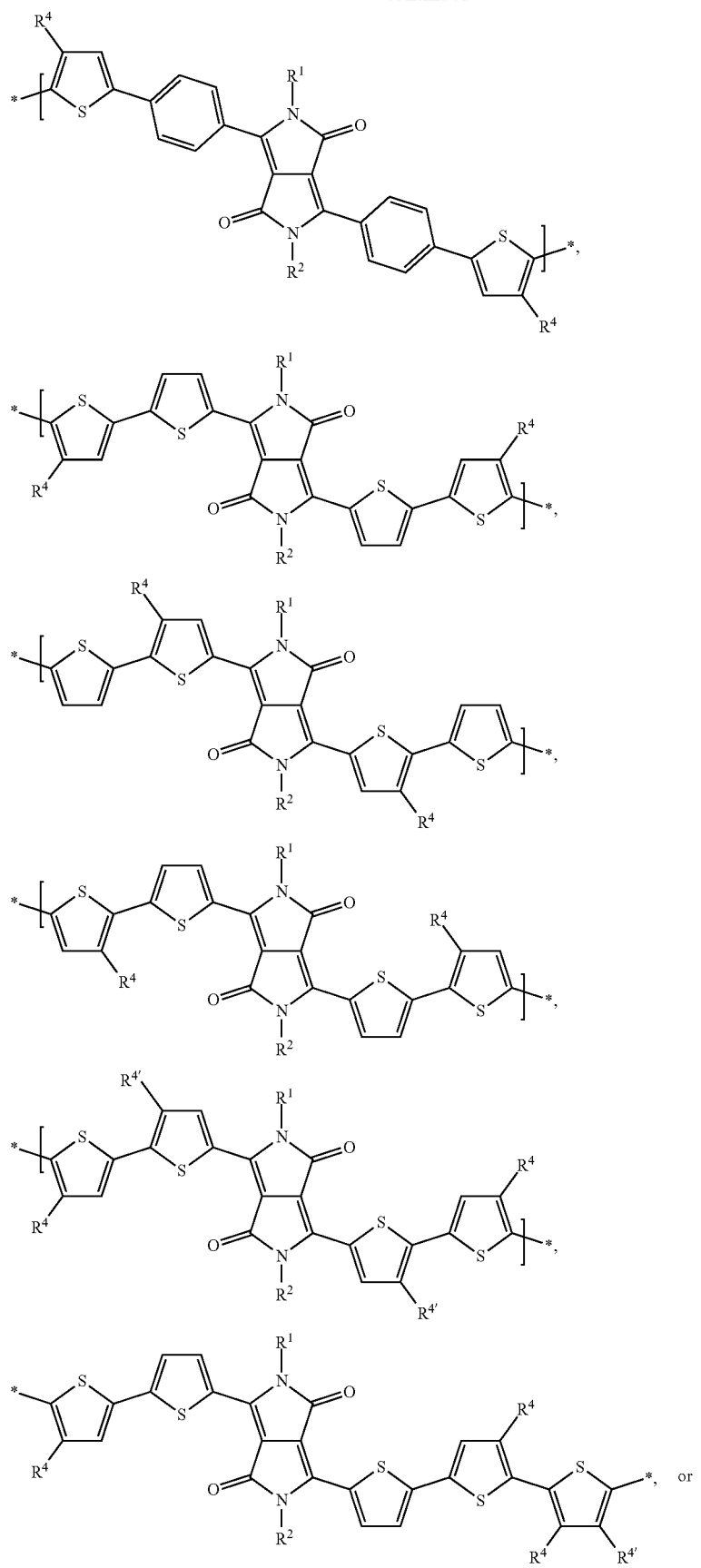

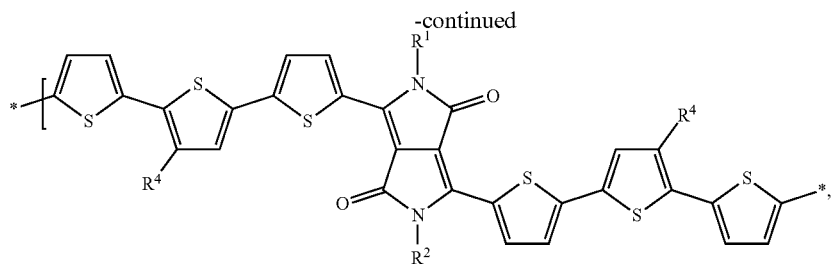

wherein $R^1$ and $R^2$ are independently from each other $C_1$-$C_{25}$alkyl, and $R^3$ and $R^{3'}$ are independently from each other $C_6$-$C_{25}$alkyl, which may optionally be interrupted by one or more oxygen atoms, $R^4$ and $R^{4'}$ are independently from each other $C_6$-$C_{25}$alkyl, which may optionally be interrupted by one or more oxygen atoms, and $R^7$ and $R^{7'}$ are independently from each other $C_6$-$C_{25}$alkyl, which may optionally be interrupted by one or more oxygen atoms.

In another preferred embodiment of the present invention the polymer is a polymer of the formula

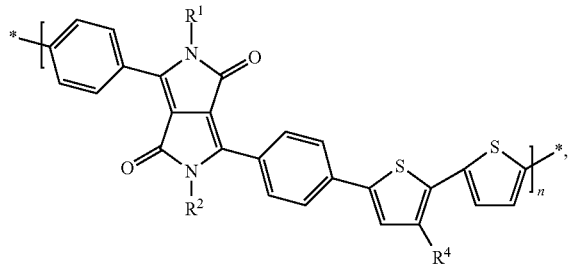

wherein $R^1$ and $R^2$ are independently from each other H, or $C_1$-$C_{25}$alkyl, and $R^4$ is $C_6$-$C_{25}$alkyl, which may optionally be interrupted by one or more oxygen atoms.

In one embodiment, the polymers according to the invention consist only of one or more type of repeating units of formula I. In a preferred embodiment, the polymers according to the invention consist of precisely one type of repeating unit of formula I (homopolymers).

According to the present invention the term "polymer" comprises polymers as well as oligomers, wherein a polymer is a molecule of high relative molecular mass, the structure of which essentially comprises the repetition of units derived, actually or conceptually, from molecules of low relative molecular mass and an oligomer is a molecule of intermediate molecular mass, the structure of which essentially comprises a small plurality of units derived, actually or conceptually, from molecules of lower relative molecular mass. A molecule is regarded as having a high relative molecular mass if it has properties which do not vary significantly with the removal of one or a few of the units. A molecule is regarded as having an intermediate molecular mass if it has properties which do vary significantly with the removal of one or a few of the units.

According to the present invention a homopolymer is a polymer derived from one species of (real, implicit, or hypothetical) monomer. Many polymers are made by the mutual reaction of complementary monomers. These monomers can readily be visualized as reacting to give an "implicit monomer", the homopolymerisation of which would give the actual product, which can be regarded as a homopolymer. Some polymers are obtained by chemical modification of other polymers, such that the structure of the macromolecules that constitute the resulting polymer can be thought of having been formed by the homopolymerisation of a hypothetical monomer.

Accordingly a copolymer is a polymer derived from more than one species of monomer, e.g. bipolymer, terpolymer, quaterpolymer, etc.

The oligomers of this invention have a weight average molecular weight of <2,000 Daltons. The polymers of this invention preferably have a weight average molecular weight of 2,000 Daltons or greater, especially 2,000 to 2,000,000 Daltons, more preferably 10,000 to 1,000,000 and most preferably 10,000 to 750,000 Daltons. Molecular weights are determined according to gel permeation chromatography using polystyrene standards.

In a preferred embodiment the polymers of the present invention are homopolymers, comprising repeating units of the formula I, which can be represented by the formula

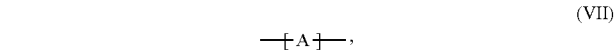 (VII)

wherein A is a repeating unit of formula I. In said aspect the polymer comprises preferably one of the repeating units of formula Ia to II, wherein repeating units of the formula Ie, Id, Ih and II are especially preferred.

Copolymers of formula VII, involving repeating units of formula I and $COM^1$ or $COM^2$ (v=0.995 to 0.005, w=0.005 to 0.995), can also be obtained by coupling reactions, such as nickel coupling reactions:

 (VIIa)

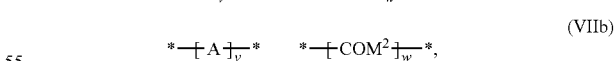 (VIIb)

wherein A is as defined above and —$COM^1$- is selected from repeating units of formula:

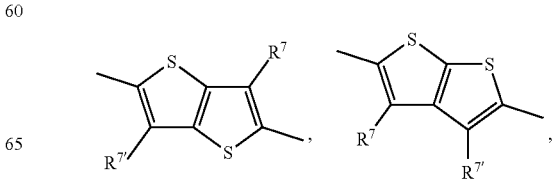

-continued

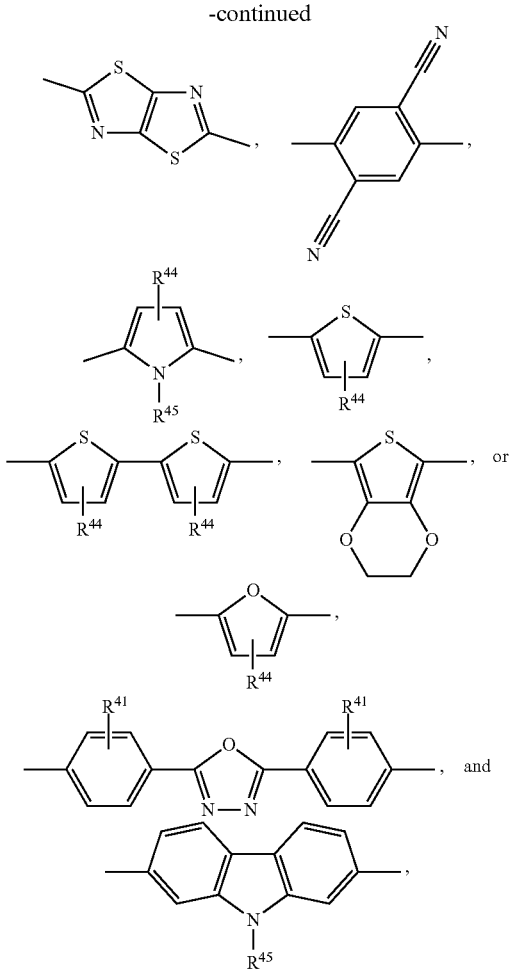

wherein $R^7$ and $R^{7'}$ are as defined above,
$R^{44}$ and $R^{41}$ are hydrogen, $C_1$-$C_{18}$alkyl, or $C_1$-$C_{18}$alkoxy, and
$R^{45}$ is H, $C_1$-$C_{18}$alkyl, or $C_1$-$C_{18}$alkyl which is substituted by E and/or interrupted by D, especially $C_1$-$C_{18}$alkyl which is interrupted by —O—, wherein D and E are as defined above, and —COM²- is a group of formula

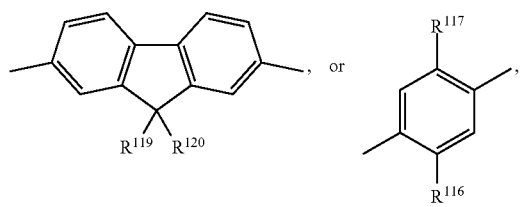

wherein
$R^{116}$ and $R^{117}$ are independently of each other H, $C_1$-$C_{18}$alkyl, which can optionally be interrupted by O, or $C_1$-$C_{18}$alkoxy, which can optionally be interrupted by O,
$R^{119}$ and $R^{120}$ are independently of each other H, $C_1$-$C_{18}$alkyl, which can optionally be interrupted by O, or
$R^{119}$ and $R^{120}$ together form a group of formula wherein
$R^{100}$ and $R^{101}$ are independently of each other H, $C_1$-$C_{18}$alkyl, or
$R^{119}$ and $R^{120}$ together form a five or six membered ring, which optionally can be substituted by $C_1$-$C_{18}$alkyl.

In said embodiment the polymer is a polymer of formula

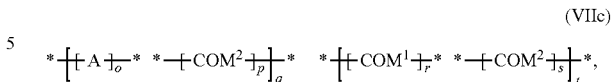
(VIIc)

wherein
A, COM¹ and COM² are as defined above,
o is 1,
p is 0, or 1,
q is 0.005 to 1,
r is 0, or 1,
s is 0, or 1, wherein e is not 1, if d is 0,
t is 0.995 to 0, wherein the sum of c and f is 1.

Homopolymers of formula VII are, for example, obtained by nickel coupling reactions, especially the Yamamoto reaction:

(VII)

wherein A is a repeating unit of formula I.

Polymerization processes involving only dihalo-functional reactants may be carried out using nickel coupling reactions. One such coupling reaction was described by Colon et al. in J. Pol. Sci., Part A, Polymer Chemistry Edition 28 (1990) 367, and by Colon et al. in J. Org. Chem. 51 (1986) 2627. The reaction is typically conducted in a polar aprotic solvent (e.g., dimethylacetamide) with a catalytic amount of nickel salt, a substantial amount of triphenylphosphine and a large excess of zinc dust. A variant of this process is described by Ioyda et al. in Bull. Chem. Soc. Jpn, 63 (1990) 80 wherein an organo-soluble iodide was used as an accelerator.

Another nickel-coupling reaction was disclosed by Yamamoto in Progress in Polymer Science 17 (1992) 1153 wherein a mixture of dihaloaromatic compounds were treated with an excess amount of nickel (1,5-cyclooctadiene) complex in an inert solvent. All nickel-coupling reactions when applied to reactant mixtures of two or more aromatic dihalides yield essentially random copolymers. Such polymerization reactions may be terminated by the addition of small amounts of water to the polymerization reaction mixture, which will replace the terminal halogen groups with hydrogen groups. Alternatively, a monofunctional aryl halide may be used as a chain-terminator in such reactions, which will result in the formation of a terminal aryl group.

Nickel-coupling polymerizations yield essentially homopolymers or random copolymers comprising DPP group-containing units and units derived from other co-monomers.

Homopolymers of formula VIId, or VIIe can be obtained, for example, by the Suzuki reaction:

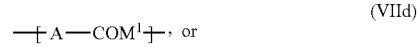
(VIId)

(VIIe)

wherein A, COM¹ and COM² are as defined above. Examples of preferred homopolymers of formula VIId, or VIIe are shown below:

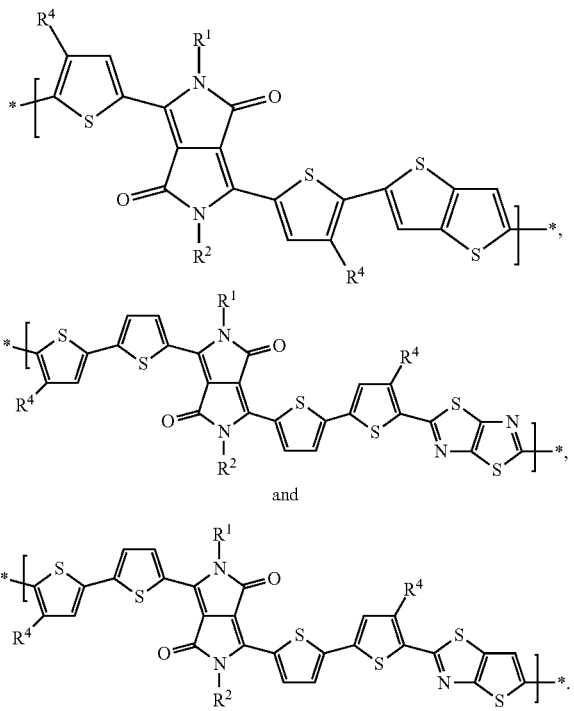

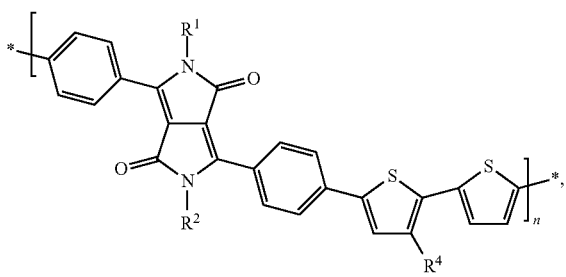

Another example of a homopolymer of formula VIId is the polymer of the formula

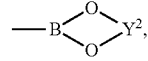

wherein $R^1$ and $R^2$ are independently from each other H, or $C_1$-$C_{25}$alkyl, and $R^4$ is $C_6$-$C_{25}$alkyl, which may optionally be interrupted by one or more oxygen atoms.

The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2', 6'-di-alkoxybiphenyl/palladium(II)acetates. An especially preferred catalyst is 2-dicyclohexylphosphino-2',6'-di-methoxybiphenyl (sPhos)/palladium(II)acetate. This reaction can be applied to preparing high molecular weight polymers and copolymers.

To prepare polymers corresponding to formula VIId, or VIIe a dihalogenide, such as a dibromide or dichloride, especially a dibromide corresponding to formula Br-A-Br is reacted with an equimolar amount of a diboronic acid or diboronate corresponding to formula

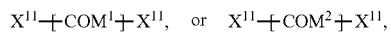

wherein $X^{11}$ is independently in each occurrence —B(OH)$_2$, —B(OY$^1$)$_2$ or $$—B\begin{array}{c}O\\O\end{array}Y^2,$$

wherein $Y^1$ is independently in each occurrence a $C_1$-$C_{10}$alkyl group and $Y^2$ is independently in each occurrence a $C_2$-$C_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —C(CH$_3$)$_2$C(CH$_3$)$_2$—, or —C(CH$_3$)$_2$CH$_2$C(CH$_3$)$_2$—, under the catalytic action of Pd and triphenylphosphine. The reaction is typically conducted at about 70° C. to 180° C. in an aromatic hydrocarbon solvent such as toluene. Other solvents such as dimethylformamide and tetrahydrofuran can also be used alone, or in mixtures with an aromatic hydrocarbon. An aqueous base, preferably sodium carbonate or bicarbonate, is used as the HBr scavenger. Depending on the reactivities of the reactants, a polymerization reaction may take 2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

If desired, a monofunctional aryl halide or aryl boronate may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

The polymers of the present invention can also be synthesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula VIId, or VIIe a dihalogenide, such as a dibromide or dichloride, especially a dibromide corresponding to formula Br-A-Br is reacted with a compound of formula

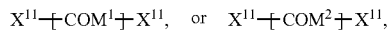

wherein $X^{11}$ is a group —SnR$^{207}$R$^{208}$R$^{209}$, in an inert solvent at a temperature in range from 0° C. to 200° C. in the presence of a palladium-containing catalyst. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using zinc reagents (A-(ZnX$^{12}$)$_2$, wherein X$^{12}$ is halogen) and halides or triflates (COM$^1$-(X$^{11}$)$_2$, wherein X$^{11}$ is halogen or triflate). Reference is, for example, made to E. Negishi et al., Heterocycles 18 (1982) 117-22.

In addition, halogen derivatives of the DPPs can be polymerized oxidatively (for example using FeCl$_3$, see, inter alia, P. Kovacic et al., Chem. Ber. 87 (1987) 357 to 379; M. Wenda et al., Macromolecules 25 (1992) 5125) or electrochemically (see, inter alia, N. Saito et al., Polym. Bull. 30 (1993) 285).

The monomers of the formula

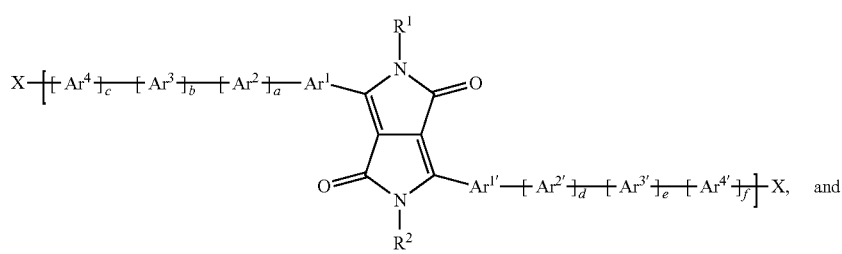

(X)

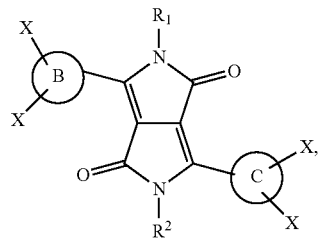

(XI)

are new and form a further aspect of the present invention, Wherein B and C are independently of each other an optionally condensed aromatic, or heteroaromatic ring, a, b, c, d, e, f, Ar$^1$, Ar$^{1'}$, Ar$^2$, Ar$^{2'}$, Ar$^3$, Ar$^{3'}$, Ar$^4$ and Ar$^{4'}$ are as defined in claim 1 and X is ZnX$^{12}$, —SnR$^{207}$R$^{208}$R$^{209}$, wherein R$^{207}$, R$^{208}$ and R$^{209}$ are identical or different and are H or C$_1$-C$_6$alkyl, wherein two radicals optionally form a common ring and these radicals are optionally branched or unbranched and X$^{12}$ is a halogen atom, very especially I, or Br; or —OS(O)$_2$CF$_3$, —OS(O)$_2$-aryl, especially

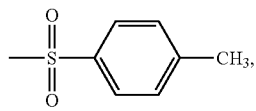

—OS(O)$_2$CH$_3$, —B(OH)$_2$, —B(OY$^1$)$_2$,

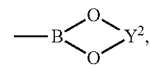

—BF$_4$Na, or —BF$_4$K, wherein Y$^1$ is independently in each occurrence a C$_1$-C$_{10}$alkyl group and Y$^2$ is independently in each occurrence a C$_2$-C$_{10}$alkylene group, such as —CY$^3$Y$^4$—CY$^5$Y$^6$—, or —CY$^7$Y$^8$—CY$^9$Y$^{10}$—CY$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a C$_1$-C$_{10}$alkyl group, especially —C(CH$_3$)$_2$C(CH$_3$)$_2$—, or —C(CH$_3$)$_2$CH$_2$C(CH$_3$)$_2$— with the proviso that, if Ar$^1$ and Ar$^{1'}$ are a group of formula

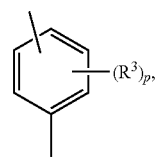

a and d are not 0 and Ar$^2$ and Ar$^{2'}$ are different from a group of formula

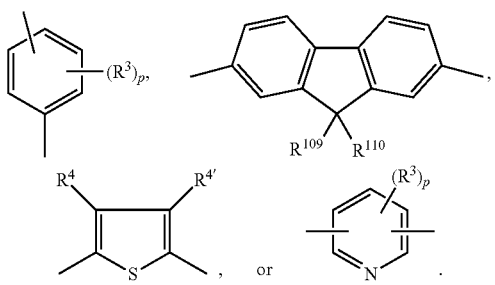

with the further proviso that, if $Ar^1$ and $Ar^{1'}$ are a group of formula

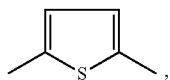

a and d are not 0.

A further aspect of the invention relates to both the oxidised and reduced form of the polymers and materials according to this invention. Either loss or gain of electrons results in formation of a highly delocalised ionic form, which is of high conductivity. This can occur on exposure to common dopants. Suitable dopants and methods of doping are known to those skilled in the art, e.g., from EP0528662, U.S. Pat. No. 5,198,153, or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I^{3-}$, $HSO_4^-$, $SO^{2-}$, $NO^{3-}$, $ClO^{4-}$, $BF^{4-}$, $PF^{6-}$, $AsF^{6-}$, $SbF^{6-}$, $FeCl^{4-}$, $Fe(CN)_6^{3-}$, anions of various sulfonic acids, such as aryl-$SO_3^-$).

When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)$ $(SbCl_6^-)$, $(NO_2^+)(BF_4^-)$, $AgClO_4$, $H_2IrCl_6$, $La(NO_3)_3.6$ $H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

Halogen is fluorine, chlorine, bromine and iodine.

$C_1$-$C_{25}$alkyl is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylhep-tyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec-butyl, isobutyl, tert-butyl.

$C_1$-$C_{25}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_2$-$C_{25}$alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_2$-$C_{24}$alkynyl is straight-chain or branched and preferably $C_2$-$C_8$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

The terms "haloalkyl, haloalkenyl and haloalkynyl" mean groups given by partially or wholly substituting the abovementioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{62}R^{63}R^{64}$, wherein $R^{62}$, $R^{63}$ and $R^{64}$ are independently of each other a $C_1$-$C_8$alkyl group, in particular a $C_1$-$C_4$ alkyl group, a $C_6$-$C_{24}$aryl group or a $C_7$-$C_{12}$aralkylgroup, such as a trimethylsilyl group.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

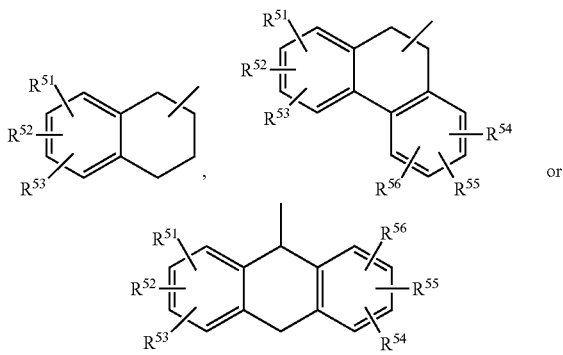

in particular

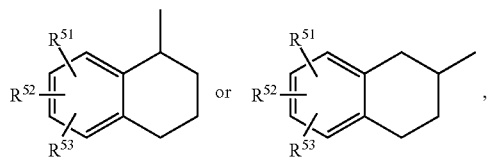

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

The term "aryl group" is typically $C_6$-$C_{24}$aryl, such as phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

The term "aralkyl group" is typically $C_7$-$C_{24}$aralkyl, such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{15}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

The term "aryl ether group" is typically a $C_{6-24}$aryloxy group, that is to say O—$C_{6-24}$aryl, such as, for example, phenoxy or 4-methoxyphenyl. The term "aryl thioether group" is typically a $C_{6-24}$arylthio group, that is to say S—$C_{6-24}$aryl, such as, for example, phenylthio or 4-methoxyphenylthio. The term "carbamoyl group" is typically a $C_{1-18}$ carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The terms "aryl" and "alkyl" in alkylamino groups, dialkylamino groups, alkylarylamino groups, arylamino groups and diarylgroups are typically $C_1$-$C_{25}$alkyl and $C_6$-$C_{24}$aryl, respectively.

Alkylaryl refers to alkyl-substituted aryl radicals, especially $C_7$-$C_{12}$alkylaryl. Examples are tolyl, such as 3-methyl-, or 4-methylphenyl, or xylyl, such as 3,4-dimethylphenyl, or 3,5-dimethylphenyl.

Heteroaryl is typically $C_2$-$C_{26}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(O$R^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H;

$C_1$-$C_8$alkylene-COO—$R^z$, e.g. $CH_2COOR^z$, $CH(CH_3)COOR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above;

$CH_2CH_2$—O—CO—CH=$CH_2$; $CH_2CH(OH)CH_2$—O—CO—C($CH_3$)=$CH_2$.

The polymers of the invention can be used as the semiconductor layer in semiconductor devices. Accordingly, the present invention also relates to semiconductor devices, comprising a polymer of the formula I. The semiconductor device is especially a diode, an organic field effect transistor and/or a solar cell, or a device containing a diode and/or an organic field effect transistor, and/or a solar cell. There are numerous types of semiconductor devices. Common to all is the presence of one or more semiconductor materials. Semiconductor devices have been described, for example, by S. M. Sze in Physics of Semiconductor Devices, 2$^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. in Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2.sup.nd edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide, or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly(vinylidene fluoride/trifluoroethylene or poly(m-xylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem. Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$ (PZT), $Bi_4Ti_3O_{12}$, $BaMgF_4$, $Ba(Zr_{1-x}Ti_x)O_3$ (BZT). In addition, alloys, hybride materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides a thin film transistor device comprising a plurality of electrically conducting gate electrodes disposed on a substrate; a gate insulator layer disposed on said electrically conducting gate electrodes; a plurality of sets of electrically conductive source and drain electrodes disposed on said insulator layer such that each of said sets is in alignment with each of said gate electrodes;

an organic semiconductor layer disposed in the channel between source and drain electrodes on said insulator layer substantially overlapping said gate electrodes; wherein said organic semiconductor layer comprise a polymer of the formula I, or a mixture containing a polymer of formula I.

The present invention further provides a process for preparing a thin film transistor device comprising the steps of:

depositing a plurality of electrically conducting gate electrodes on a substrate;

depositing a gate insulator layer on said electrically conducting gate electrodes;

depositing a plurality of sets of electrically conductive source and drain electrodes on said layer such that each of said sets is in alignment with each of said gate electrodes;

depositing a layer of a polymer of the formula I on said insulator layer such that said layer of the compound of formula I, or a mixture containing a polymer of formula I, substantially overlaps said gate electrodes; thereby producing the thin film transistor device.

A mixture containing a polymer of formula I results in a semi-conducting layer comprising a polymer of formula I (typically 5% to 99.9999% by weight, especially 20 to 85% by weight) and at least another material. The other material can be, but is not restricted to a fraction of the same polymer of formula I with different molecular weight, another polymer of formula I, a semi-conducting polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

For heterojunction solar cells the active layer comprises preferably a mixture of a polymer of formula I and a fullerene, such as [60]PCBM (=6,6-phenyl-C61-butyric acid methyl ester), or [70]PCBM, in a weight ratio of 1:1 to 1:3.

Any suitable substrate can be used to prepare the thin films of the polymers of the present invention. Preferably, the substrate used to prepare the above thin films is a metal, silicon, plastic, paper, coated paper, fabric, glass or coated glass.

Alternatively, a TFT is fabricated by, for example, by solution deposition of a polymer on a highly doped silicon substrate covered with a thermally grown oxide layer followed by vacuum deposition and patterning of source and drain electrodes.

In yet another approach, a TFT is fabricated by deposition of source and drain electrodes on a highly doped silicon substrate covered with a thermally grown oxide and then solution deposition of the polymer to form a thin film.

The gate electrode could also be a patterned metal gate electrode on a substrate or a conducting material such as, a conducting polymer, which is then coated with an insulator applied either by solution coating or by vacuum deposition on the patterned gate electrodes.

Any suitable solvent can be used to dissolve, and/or disperse the polymers of the present application, provided it is inert and can be removed partly, or completely from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers amides, such as chloroform, tetrachloroethane, tetrahydrofuran, toluene, tetraline, anisole, xylene, ethyl acetate, methyl ethyl ketone, dimethyl formamide, dichlorobenzene, trichlorobenzene, propylene glycol monomethyl ether acetate (PGMEA) and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising the semiconductor material of the present invention, which is not fully dissolved in a solvent. The dispersion can be done selecting a composition including at least a polymer of formula I, or a mixture containing a polymer of formula I, and a solvent, wherein the polymer exhibits lower solubility in the solvent at room temperature but exhibits greater solubility in the solvent at an elevated temperature, wherein the composition gels when the elevated temperature is lowered to a first lower temperature without agitation;

dissolving at the elevated temperature at least a portion of the polymer in the solvent;

lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a polymer of formula I, or a mixture containing a polymer of formula I of the present invention.

The degree of solubility of the polymer of formula I in the solvent may vary for example from 0% to about 20% solubility, particularly from 0% to about 5% solubility.

Preferably, the thickness of the organic semiconductor layer is in the range of from about 5 to about 1000 nm, especially the thickness is in the range of from about 10 to about 100 nm.

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, ink jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like. Due to its ambipolarity the material can also be used in Organic Light Emitting Transistors (OLET).

The invention provides organic photovoltaic (PV) devices (solar cells) comprising a polymer according to the present invention.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor.

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another polymer of formula I or any semi-conducting polymer provided that the polymers retain acceptor-type and electron mobility characteristics, organic small molecules, carbon nanotubes, inorganic particles (quantum dots, quantum rods, quantum tripods, $TiO_2$, ZnO etc.).

The electrodes are preferably composed of metals or "metal substitutes". Herein the term "metal" is used to embrace both materials composed of an elementally pure metal, e.g., Mg, and also metal alloys which are materials composed of two or more elementally pure metals, e.g., Mg and Ag together, denoted Mg:Ag. Here, the term "metal substitute" refers to a material that is not a metal within the normal definition, but which has the metal-like properties that are desired in certain appropriate applications. Commonly used metal substitutes for electrodes and charge transfer layers would include doped wide-bandgap semiconductors, for example, transparent conducting oxides such as indium tin oxide (ITO), gallium indium tin oxide (GITO), and zinc indium tin oxide (ZITO). Another suitable metal substitute is the transparent conductive polymer polyanaline (PANI) and its chemical relatives, or PEDOT:PSS. Metal substitutes may be further selected from a wide range of non-metallic materials, wherein the term "non-metallic" is meant to embrace a wide range of materials provided that the material is free of metal in its chemically uncombined form. Highly transparent, non-metallic, low resistance cathodes or highly efficient, low resistance metallic/non-metallic compound cathodes are, for example, disclosed in U.S. Pat. Nos. 6,420,031 and 5,703,436.

The substrate can be, for example, a plastic (flexible substrate), or glass substrate.

In another preferred embodiment of the invention, a smoothing layer is situated between the anode and the photoactive layer. A preferred material for this smoothing layer comprises a film of 3,4-polyethylenedioxythiophene (PEDOT), or 3,4-polyethylenedioxythiophene:polystyrene-sulfonate (PEDOT:PSS).

In a preferred embodiment of the present invention, the photovoltaic cell comprises, as described for example, in U.S. Pat. No. 6,933,436B a transparent glass carrier, onto which an electrode layer made of indium/tin oxide (ITO) is applied. This electrode layer generally has a comparatively rough surface structure, so that it is covered with a smoothing layer made of a polymer, typically PEDOT, which is made electrically conductive through doping. The photoactive layer is made of two components, has a layer thickness of, for example, 100 nm to a few gm depending on the application method, and is applied onto this smoothing layer. Photoactive layer is made of a conjugated polymer of the present invention, as an electron donor and a fullerene, particularly functionalized fullerene PCBM, as an electron acceptor. These two components are mixed with a solvent and applied as a solution onto the smoothing layer by, for example, the spin-coating method, the casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethylsulfoxide, chlorobenzene, 1,2-dichlorobenzene and mixtures thereof.

Before a counter electrode is applied, a thin transition layer, which must be electrically insulating, having a layer thickness of, for example, 0.6 nm, is applied to photoactive layer 4. In this exemplary embodiment, this transition layer is made of an alkali halogenide, namely a lithium fluoride, which is vapor deposited in a vacuum of $2 \cdot 10^{-6}$ torr at a rate of 0.2 nm/minute.

If ITO is used as a hole-collecting electrode, aluminum, which is vapor deposited onto the electrically insulating transition layer, is used as an electron-collecting electrode. The electric insulation properties of the transition layer obviously prevent influences which hinder the crossing of the charge carrier from being effective, particularly in the transition region from the photoactive layer to the transition layer.

In a further embodiment on the invention, one or more of the layers may be treated with plasma prior to depositing the next layer. It is particularly advantageous that the PEDOT:PSS layer be subject to a mild plasma treatment prior to deposition of the next layer.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the inventive compounds, materials or films can also be used alone or together with other materials in or as alignment layers in LCD or OLED devices, as described for example in US2003/0021913.

The following examples are included for illustrative purposes only and do not limit the scope of the claims. Unless otherwise stated, all parts and percentages are by weight. Weight-average molecular weight ($M_w$) and polydispersity ($M_w/M_n$=PD) are determined by Gel Permeation Chromatography (GPC) [Apparatus: GPC$_{max}$+TDA 302 from Viscotek (Houston, Tex., USA) yielding the responses form refractive index (RI), low angle light scattering (LALS), right angle light scattering (RALS) and differential viscosity (DP) measurements. Chromatographic conditions: Column: PL$_{gel}$ mixed C (300×7.5 mm, 5 μm particles) covering the molecular weight range from about $1\times10^3$ to about $2.5\times10^6$ Da from Polymer Laboratories (Church Stretton, UK); Mobile phase: tetrahydrofuran containing 5 g/l of sodium trifluoroacetate; Mobile phase flow: either 0.5 or 0.7 ml/min; Solute concentration: about 1-2 mg/ml; Injection volume: 100 μl; Detection: RI, LALS, RALS, DP. Procedure of molecular weight calibration: Relative calibration is done by use of a set of 10 polystyrene calibration standards obtained from Polymer Laboratories (Church Stretton, UK) spanning the molecular weight range from 1'930'000 Da-5'050 Da, i. e., PS 1'930'000, PS 1'460'000, PS 1'075'000, PS 560'000, PS 330'000, PS 96'000, PS 52'000, PS 30'300, PS 10'100, PS 5'050 Da. Absolute calibration is done on the base of the responses of LALS, RALS and DP. As experienced in a large number of investigations this combination provides optimum calculation of molecular weight data. Usually PS 96'000 is used as the molecular weight calibration standard, but in general every other PS standard lying in the molecular weight range to be determined can be chosen for this purpose.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

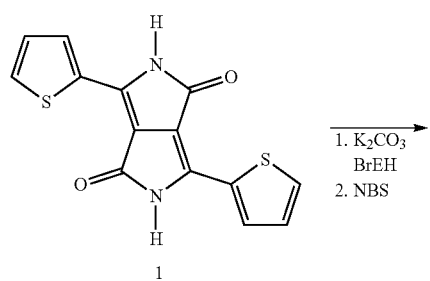

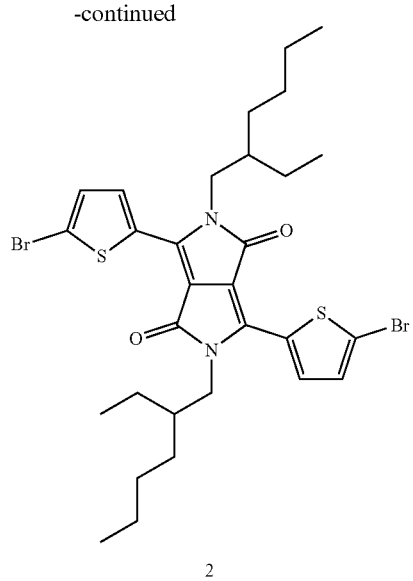

a) A solution of 4.5 g of DPP 1, 6.23 g of $K_2CO_3$ and 8.68 g of 1-bromo-2-ethyl-hexyl in 60 ml of N-methyl-pyrrolidone (NMP) is heated to 140° C. for 6 h. The mixture is washed with water and extracted with dichloromethane. The organic phase is then dried and filtered on a double layer of silica gel and Hyflo® (CAS 91053-39-3; Fluka 56678) before it is concentrated. The residue is dissolved in 100 ml of chloroform, cooled down to 0° C. and 2 equivalents of N-bromosuccinimide are then added portion wise over a period of 1 h. After the reaction has been completed, the mixture is washed with water. The organic phase is extracted, dried and concentrated. The compound is then purified over a silica gel column to give 1.90 g of a violet powder of DPP 2.

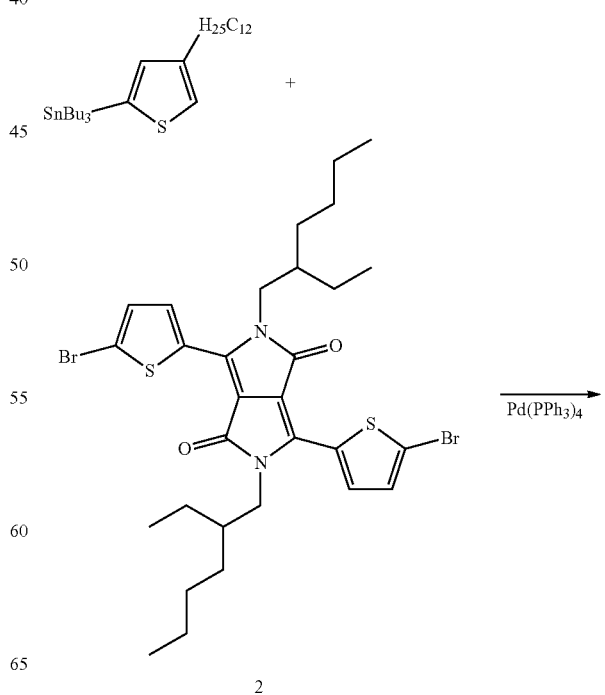

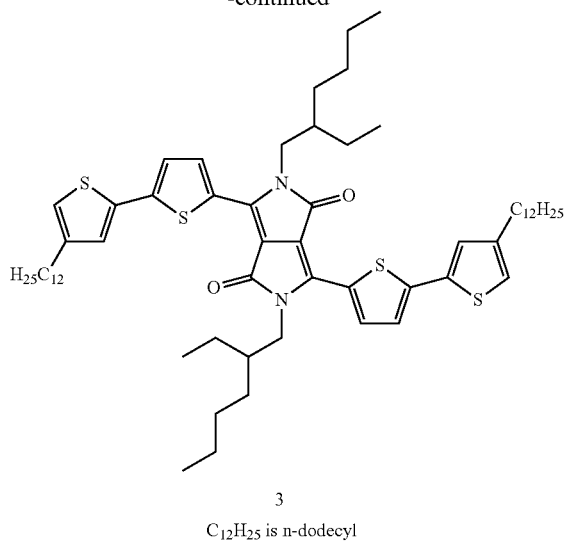

3

$C_{12}H_{25}$ is n-dodecyl b) A solution of 500 mg of the dibrominated DPP 2, 990 mg of the tin derivative and 85 mg of $Pd(PPh_3)_4$ in 30 ml of dry toluene is refluxed overnight under inert conditions. After cooling down, the mixture is filtrated on a double layer silica gel/Hyflo®, concentrated and precipitated with methanol. The precipitate is filtrated and rinsed with methanol to give 530 mg of a blue solid of DPP 3.

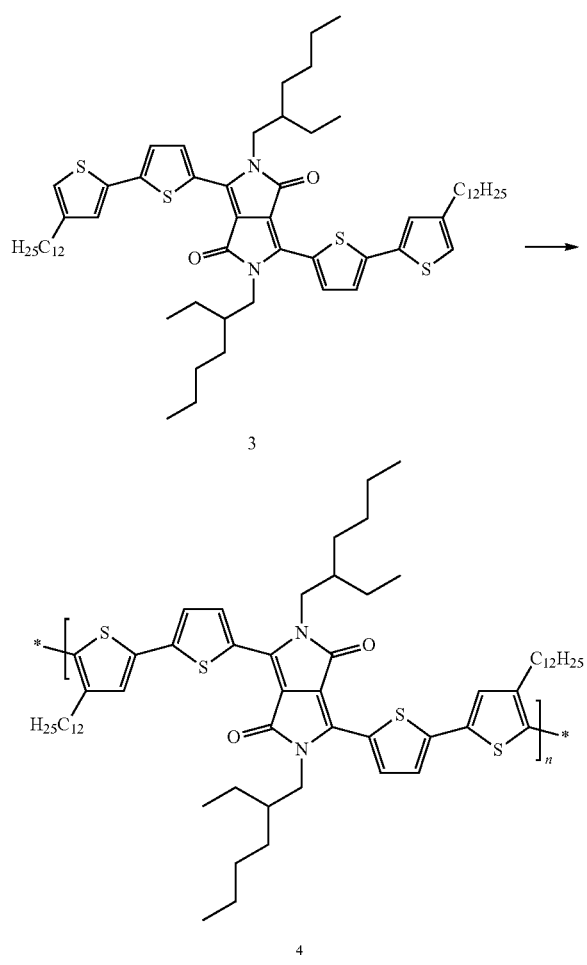

c) A solution of 2.55 g of the corresponding monomer 3 in chlorobenzene is degassed with argon over 15 min at 50° C. Then 1.6 g of $FeCl_3$ are added in nitromethane and the mixture is stirred while degassing for 4 hours at 50° C. The solution is then poured into methanol and the blue precipitate is then filtrated and washed with methanol. The solid is then purified by soxhlet extraction, using methanol and hexane to purify and chloroform to extract 2 g of the polymer fraction (4).

$M_w$=13301

Fe content=75 ppm

Photophysical Properties:

UV spectra of spin coated films on glass substrates are made from hot chlorobenzene solutions and annealed at different temperatures:

| Annealing Conditions | UV/Vis-absorption |
| --- | --- |
| Room temperature | 680 nm |
| 20 minutes at 100° C. | 720 nm, 800 nm |
| 20 minutes at 150° C. | 720 nm, 800 nm |

Growing of the band at 800 nm shows the appearance of strong aggregation behaviour while annealing.

Application Example 1a

DPP-Polymers Based Field-Effect Transistors a) Experimental:

Bottom-gate thin-film transistor (TFT) structures with p-Si gate were used for all experiments. A high-quality thermal $SiO_2$ layer served as gate-insulator of $C_i$=32.6 $nF/cm^2$ capacitance per unit area. Source and drain electrodes were patterned by photolithography directly on the gate-oxide (bottom-contact configuration). On each substrate 16 transistors are present with Au source/drain electrodes defining channels of different length. Prior to the deposition of the organic semiconductor the $SiO_2$ surface was derivatized with hexamethyldisilazane (HMDS) or octadecyltrichlorosilane (OTS). The films are prepared either by spin casting or drop casting the polymer obtained in example 1 in different solvents. The transistor behaviour is measured on an automated tester elaborated by CSEM, Transistor Prober TP-10.

b) Transistor Performance:

The thin-film transistors showed clear p-type transistor behavior. From a linear fit to the square root of the saturated transfer characteristics a field-effect mobility of 0.15 $cm^2/Vs$ could be determined. The transistors showed a threshold voltage of about 0 V to 5 V. The transistors showed good on/off current ratios of $10^4$ to $10^7$.

Annealing of the sample results in a drastic increase of the performances (especially mobility), which can be correlated to a better aggregation of the polymer in the solid state. Testing of a set of OFETs after 2 months exposed in air conditions shows remarkable stability as the mobility is almost constant. The on/off ratio, which usually suffers the most, is only reduced by a factor of 10.

Application Example 1b

DPP-Polymer Based Bulk Heterojunction Solar Cell a) Experimental:

The solar cell has the following structure: Al electrode/ LiF layer/organic layer, including polymer of the invention/ [poly(3,4-ethylenedioxy-thiophene) (PEDOT)/poly(styrene-sulfonic acid) (PSS)]/ITO electrode/glass substrate. The solar cells are made by spin-coating a layer of PEDOT-PSS on a pre-patterned ITO on glass substrate. Then a 1:4 mixture of the polymer of example 1 (0.5% by weight): [60]PCBM (a substituted $C_{60}$ fullerene:

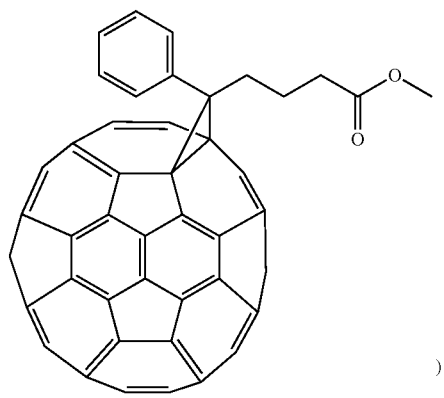 [SMILES: COC(=O)CCCC1(c2ccccc2)C23C=Cc4cc5c6c7c4C21c1c2c4c(cc8ccc9cc(c6c6c9c8c4c6c17)C5)CC2=C3]

is spin coated (organic layer). LiF and Al are sublimed under high vacuum through a shadow-mask.

b) Solar Cell Performance:

The solar cell is measured under a solar light simulator. Then with the External Quantum Efficiency (EQE) graph the current is estimated under AM1.5 conditions.

This leads to value of $J_{sc}$=4.1 mA/cm², FF=0.539 and $V_{oc}$=0.733 V for an estimated overall efficiency of 1.62% measured before annealing. After 10 min at 100° C. the estimated efficiency grows to 2%. After optimisation of the morphology of the active layer by varying the deposition solvent, the polymer/[60]PCBM ratio etc. the performance of the device can be pushed up to 3.06% ($J_{sc}$=9.5 mA/cm², FF=0.46 and $V_{oc}$=0.7 V).

Example 2

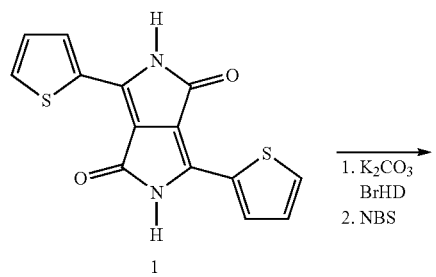

1

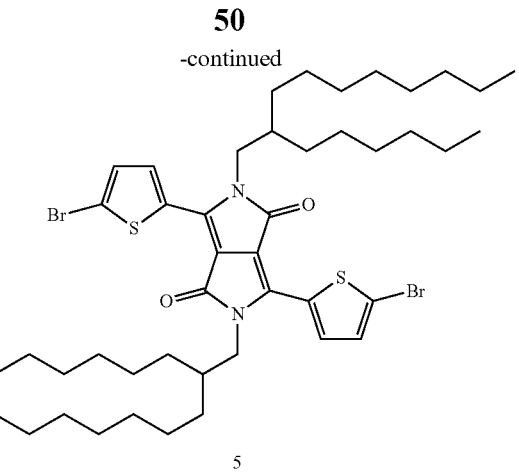

5

A solution of 25 g of DPP 1, 46.07 g of $K_2CO_3$ and 75 g of 1-bromo-2-hexyl-decyl in 300 ml of N-methyl-pyrrolidone (NMP) is heated to 140° C. for 6 h. The mixture is washed with water and extracted with dichloromethane. The organic phase is then dried and filtered on a double layer of silica gel and Hyflo® before it is concentrated. The residue is dissolved in 100 ml of chloroform, cooled down to 0° C. and 2 equivalents of N-bromosuccinimide are then added portion wise over a period of 1 h. After the reaction has been completed, the mixture is washed with water. The organic phase is extracted, dried and concentrated. The compound is then purified over a silica gel column to give 19 g of a violet powder of DPP 5.

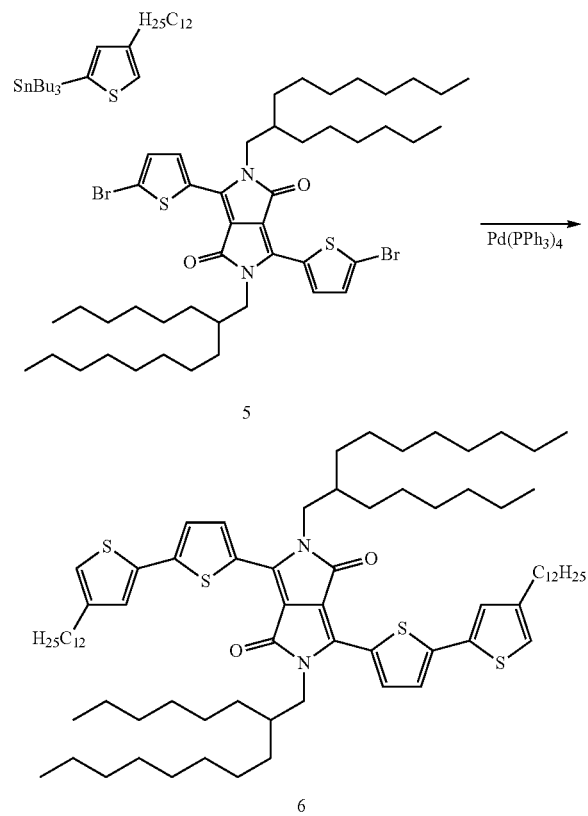

b) A solution of 18.5 g of the dibrominated DPP 5, 27.47 g of the tin derivative and 2.36 g of Pd(PPh$_3$)$_4$ in 250 ml of dry toluene is refluxed overnight under inert conditions. After cooling down, the mixture is purified on a silica gel column (CHCl₃/hexane 3/7) to give 20.2 g of a blue solid of DPP 6.

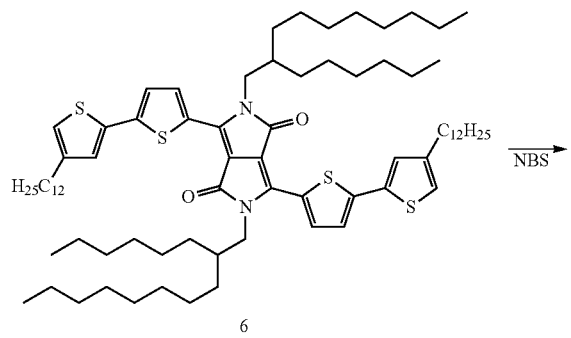

6

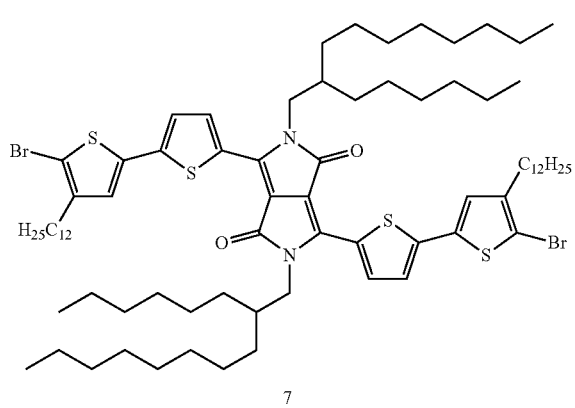

7 c) A solution of 10 g of the DPP derivative 6 is dissolved in 300 ml of chloroform, cooled down to 0° C. and 2 equivalents of N-bromosuccinimide are then added portion wise over a period of 1 h. After the reaction is completed, the mixture is washed with water. The organic phase is extracted, dried, concentrated and precipitated with methanol. The precipitate is filtered and rinsed with methanol to give 10 g of a blue solid of DPP 7.

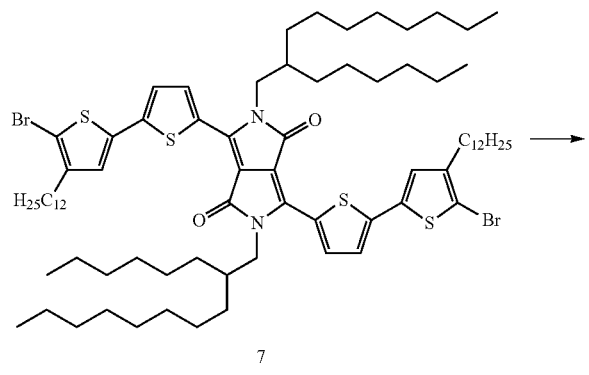

7

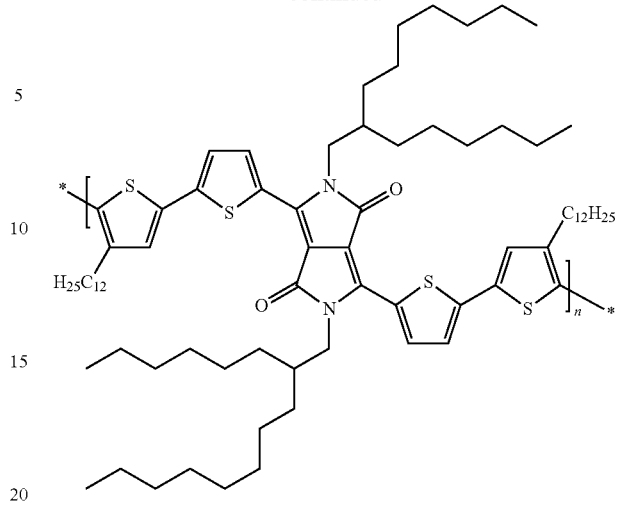

In a shlenk tube, a solution of 240 mg of Ni(COD)₂ and 140 mg bipyridine in 10 ml of toluene is degassed for 15 min. 1 g of the corresponding dibrominated monomer 7 is added to this solution and then the mixture is heated to 80° C. and stirred vigorously overnight. The solution is poured on 100 ml of a 1/1/1 methanol/HCl/acetone mixture and stirred for 1 h. The precipitate is then filtered, dissolved in CHCl₃ and stirred vigorously at 60° C. with an aqueous solution of ethylenediaminetetraacetic acid (EDTA) tetrasodium salt for one additional hour. The organic phase is washed with water, concentrated and precipitated in methanol. The residue is purified by soxhlet extraction using methanol and hexane and the polymer is then extracted with CHCl₃ to give 250 mg of purple fibres.

$M_w$=77465

Ni content=65 ppm

Solubility>10% by weight in toluene

Photophysical Properties:

UV of spin coated film on glass substrate is made from a hot chlorobenzene solution and annealed at different temperatures:

| Annealing Conditions | UV/Vis-absorption |
| --- | --- |
| Room temperature | 680 nm |
| 20 minutes at 100° C. | 720 nm, 800 nm |

Growing of the band at 800 nm shows the appearance of strong aggregation behaviour while annealing.

Application Example 2a

DPP-Polymers Based Field-Effect Transistors a) Experimental:

Application Example 1a is repeated, except that instead of the polymer obtained in example 1 the polymer obtained in example 2 is used.

b) Transistor Performance:

The thin-film transistors showed clear p-type transistor behavior. From a linear fit to the square root of the saturated transfer characteristics a field-effect mobility up to 0.013 cm²Ns could be determined. The transistors showed a threshold voltage of about 0 V to 4 V. The transistors showed good on/off current ratios of $10^5$ to $10^7$. Testing of a set of OFETs after 7 days exposed in air conditions shows remarkable stability as the mobility is almost constant even better, on/off ratio which usually suffers the most is only reduced by a factor of 5. This compound shows an electron mobility up to $10^{-3}$ cm$^2$Ns on the normal setup. After optimisation of this setup using top contact transistors, the ambi-polarity of this polymer is even more pronounced with similar mobilites for holes and electrons up to 0.1 cm$^2$Ns.

Example 3

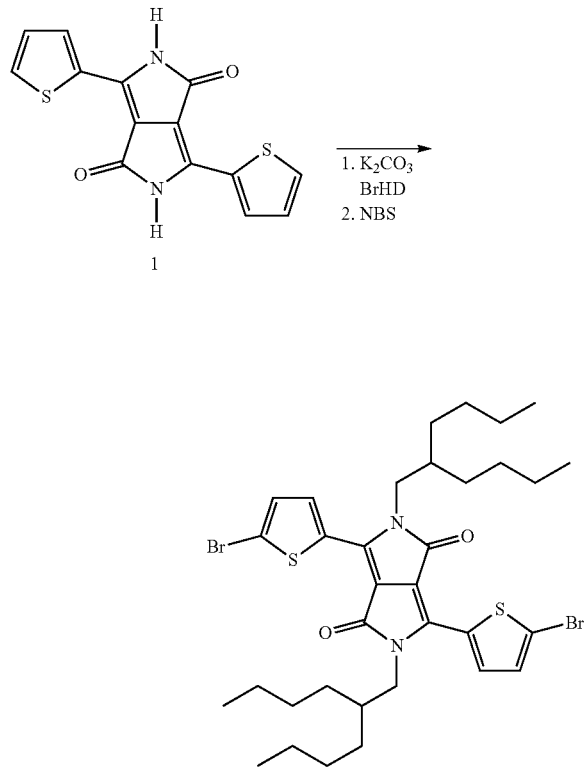

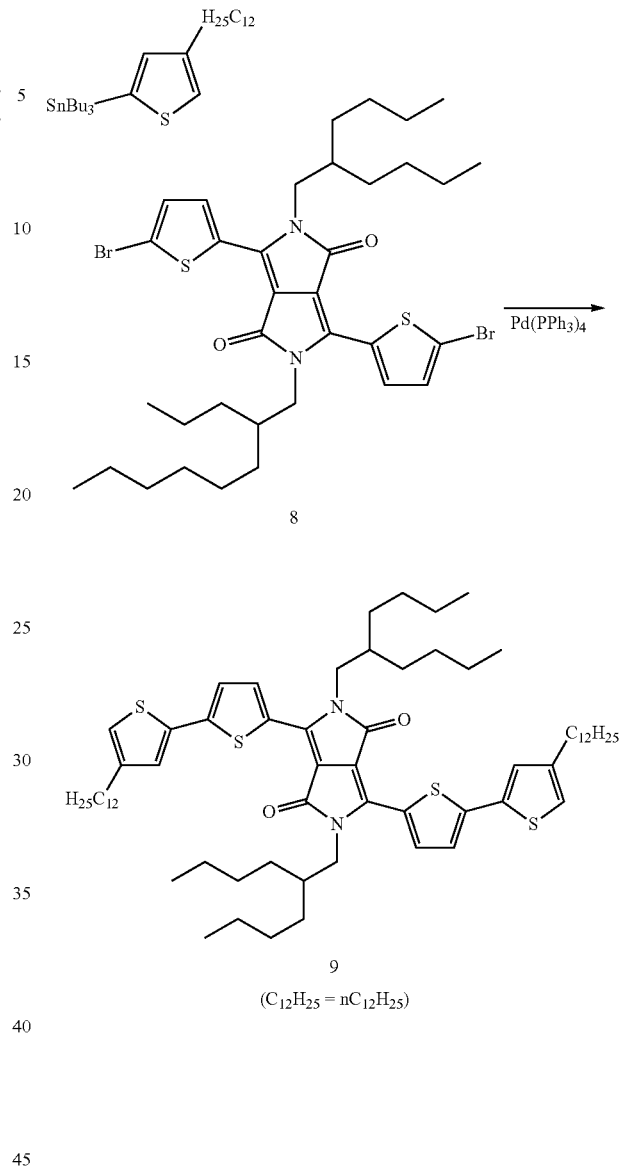

a) A solution of 25 g of DPP 1, 46.07 g of $K_2CO_3$ and 55 g of 1-bromo-2-butyl-hexyl in 300 ml of N-methyl-pyrrolidone (NMP) is heated to 140° C. for 6 h. The mixture is washed with water and extracted with dichloromethane. The organic phase is then dried and filtered on a double layer of silica gel and Hyflo® before it is concentrated. The residue is dissolved in 100 ml of chloroform, cooled down to 0° C. and 2 equivalents of N-bromosuccinimide are then added portion wise over a period of 1 h. After the reaction has been completed, the mixture is washed with water. The organic phase is extracted, dried and concentrated. The compound is then purified over a silica gel column to give 9.5 g of a violet powder of DPP 8.

b) A solution of 2.24 g of the dibrominated DPP 8, 4.11 g of the tin derivative and 351 mg of Pd(PPh$_3$)$_4$ in 50 ml of dry toluene is refluxed overnight under inert conditions. After cooling down, the mixture is purified on a silica gel column (CHCl$_3$/hexane 3/7) to give 2.37 g of a blue solid of DPP 9.

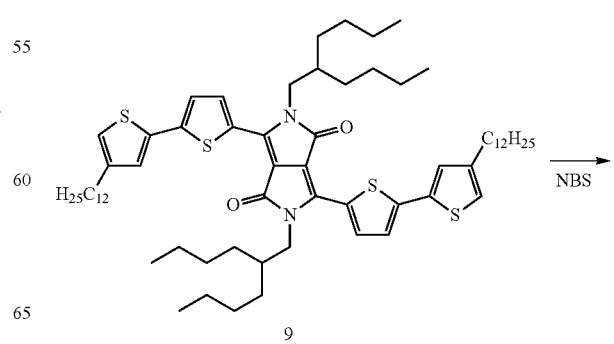

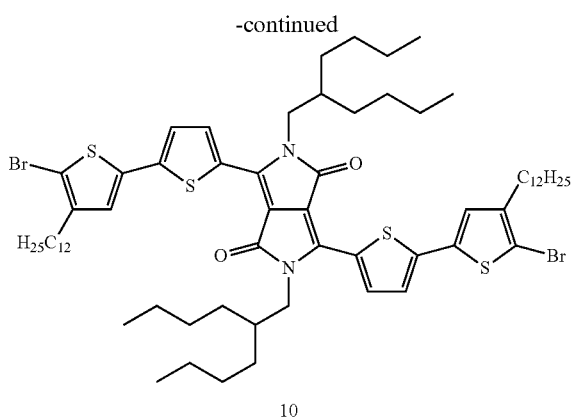

c) A solution of 1.27 g of the DPP derivative 9 is dissolved in 60 ml of chloroform, cooled down to 0° C. and 2 equivalents of N-bromosuccinimide are then added portion wise over a period of 1 h. After the reaction is completed, the mixture is washed with water. The organic phase is extracted, dried, concentrated and precipitated with methanol. The precipitate is filtrated and rinsed with methanol to give 1.32 g of a blue solid of DPP 10.

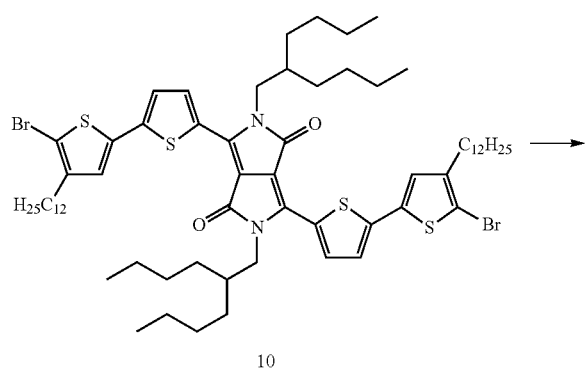

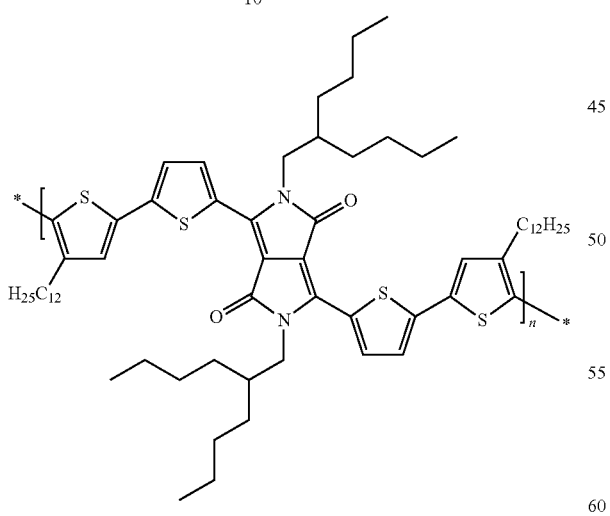

d) In a Schlenk tube, a solution of 244 mg of Ni(COD)$_2$ and 142 mg bipyridine in 10 ml of toluene is degassed for 15 min. 1 g of the corresponding dibrominated monomer 10 is added to this solution and then the mixture is heated to 80° C. and stirred vigorously overnight. The solution is poured on 100 ml of a 1/1/1 methanol/HCl/acetone mixture and stirred for 1 h. The precipitate is then filtrated, dissolved in CHCl$_3$ and stirred vigorously at 60° C. with an aqueous solution of ethylenediaminetetraacetic acid (EDTA) tetrasodium salt for one additional hour. The organic phase is washed with water, concentrated and precipitated in methanol. The residue is purified by soxhlet extraction using methanol and hexane and the polymer is then extracted with CHCl$_3$ to give 650 mg of purple fibres.

$M_w$=30000

Ni content=52 ppm

Solubility=0.5% by weight in CHCl$_3$

Photophysical Properties:

UV of spin coated film on glass substrate is made from a hot chlorobenzene solution and annealed at different temperatures:

| Annealing Conditions | UV/Vis-absorption |
| --- | --- |
| Room temperature | 720 nm, 810 nm |

The band at 810 nm is attributed to the aggregation behaviour.

Application Example 3

DPP-Polymers Based Field-Effect Transistors a) Experimental:

Application Example 1a is repeated, except that instead of the polymer obtained in example 1 the polymer obtained in example 3 is used.

b) Transistor Performance:

The thin-film transistors showed clear p-type transistor behaviour. From a linear fit to the square root of the saturated transfer characteristics a field-effect mobility up to 0.1 cm$^2$/Vs could be determined. The transistors showed a threshold voltage of about 6 V. The transistors showed good on/off current ratios of $10^4$ to $10^5$.

Example 4

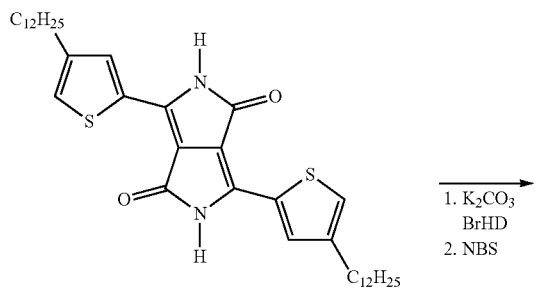

-continued

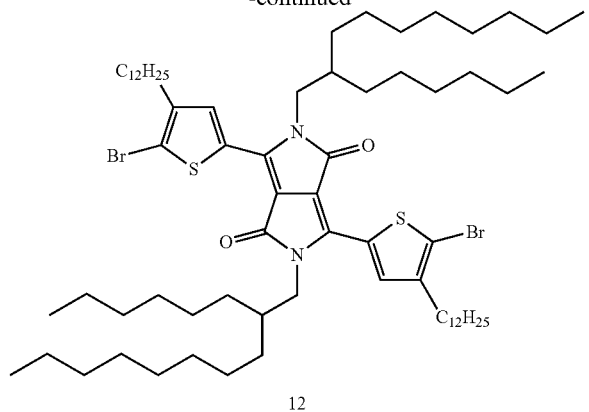

12 a) A solution of 3.5 g of DPP 11, 3.04 g of $K_2CO_3$ and 4.13 g of 1-bromo-2-hexyl-decyl in 60 ml of N-methyl-pyrrolidone (NMP) is heated to 140° C. for 6 h. The mixture is washed with water and extracted with dichloromethane. The organic phase is then dried and filtered on a double layer of silica gel and Hyflo® before it is concentrated. The residue is dissolved in 100 ml of chloroform, cooled down to 0° C. and 2 equivalents of N-bromosuccinimide are then added portion wise over a period of 1 h. After the reaction has been completed, the mixture is washed with water. The organic phase is extracted, dried and concentrated. The compound is then purified over a silica gel column to give 1.7 g of a violet powder of DPP 12.

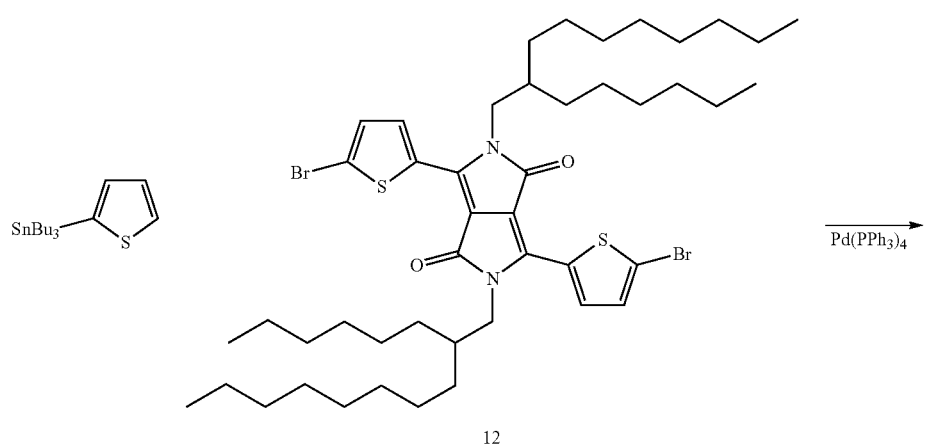

12

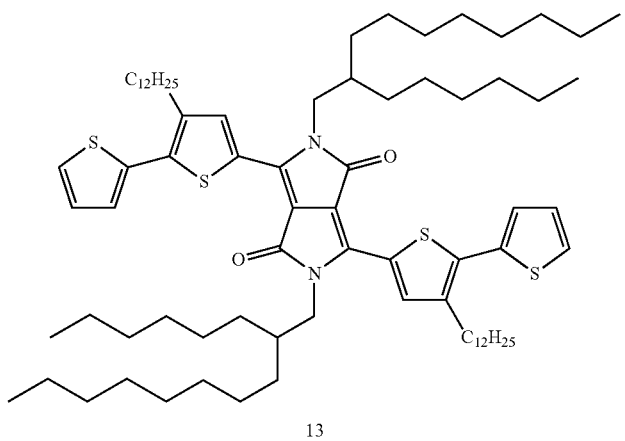

13 b) A solution of 1.6 g of the dibrominated DPP 12, 0.65 g of the tin derivative and 150 mg of Pd(PPh$_3$)$_4$ in 60 ml of dry toluene is refluxed overnight under inert conditions. After cooling down, the mixture is purified on a silica gel column (CHCl$_3$/hexane 3/7) to give 1.27 g of a blue solid of DPP 13.

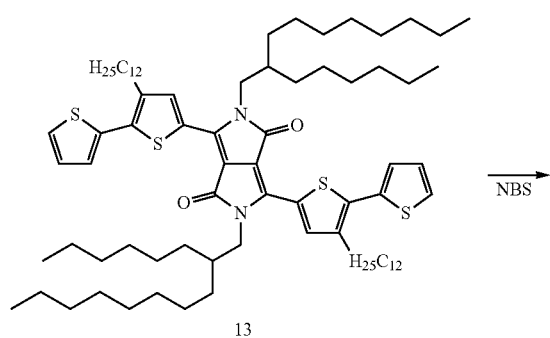

13

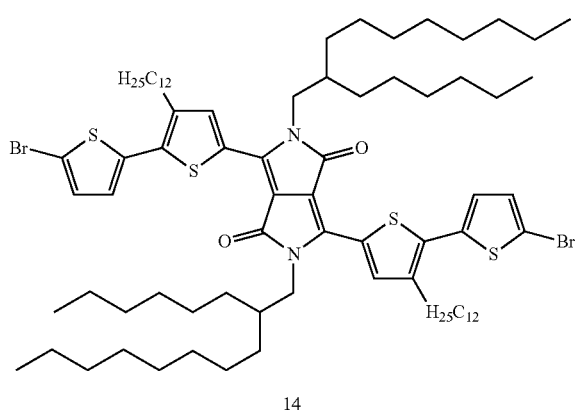

14 c) A solution of 1.27 g of the DPP derivative 13 is dissolved in 50 ml of chloroform, cooled down to 0° C. and 2 equivalents of N-bromosuccinimide are then added portion wise over a period of 1 h. After the reaction is completed, the mixture is washed with water. The organic phase is extracted, dried, concentrated and precipitated with methanol. The precipitate is filtrated and rinsed with methanol to give 1.22 g of a blue solid of DPP 14.

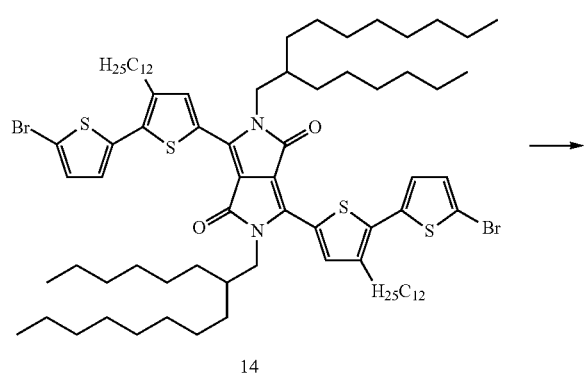

14

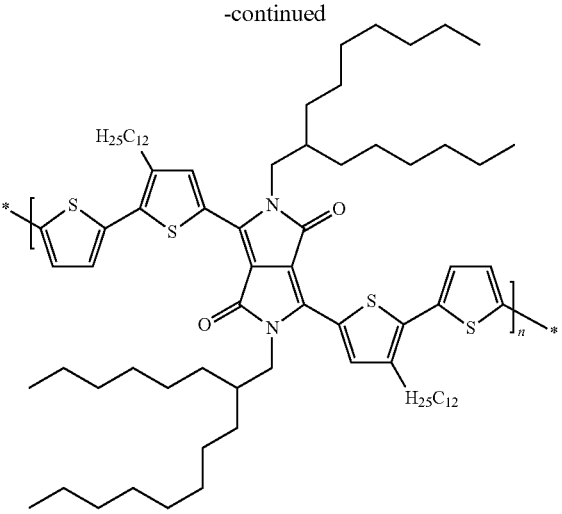

d) In a Schlenk tube, a solution of 292 mg of Ni(COD)$_2$ and 170 mg bipyridine in 10 ml of toluene is degassed for 15 min. 1.2 g of the corresponding dibrominated monomer 14 is added to this solution and then the mixture is heated to 65° C. and stirred vigorously for 41 h. The solution is poured on 100 ml of a 1/1/1 methanol/HCl/acetone mixture and stirred for 1 h. The precipitate is then filtrated, dissolved in CHCl$_3$ and stirred vigorously at 60° C. with an aqueous solution of ethylenediaminetetraacetic acid (EDTA) tetrasodium salt for one additional hour. The organic phase is washed with water, concentrated and precipitated in methanol. The residue is purified by soxhlet extraction using methanol and hexane and the polymer is then extracted with CHCl$_3$ to give 730 mg of purple fibres.

$M_w$=30000
Ni content=14 ppm
Solubility=0.5% by weight in CHCl$_3$
Photophysical Properties:
UV of spin coated film on glass substrate is made from a hot chlorobenzene solution and annealed at different temperatures:

| Annealing Conditions | UV/Vis-absorption |
| --- | --- |
| Room temperature | 720 nm, 800 nm |

The band at 800 nm is attributed to the aggregation behaviour.

Application Example 4

DPP-Polymers Based Field-Effect Transistors a) Experimental:
Application Example 1a is repeated, except that instead of the polymer obtained in example 1 the polymer obtained in example 4 is used.

b) Transistor Performance:
The thin-film transistors showed clear p-type transistor behaviour. From a linear fit to the square root of the saturated transfer characteristics a field-effect mobility up to 0.013 cm$^2$Ns could be determined. The transistors showed a threshold voltage of about 4 V to 8 V. The transistors showed good on/off current ratios of $10^4$ to $10^5$. Testing of a set of OFETs after 2 months exposed in air conditions shows remarkable stability as the mobility is even better (up to 0.028 cm²/Vs), on/off ratio which usually suffer the most is also increased by a factor of 5 to 10 and threshold voltage in the range of 0 V to 4 V.

Example 5

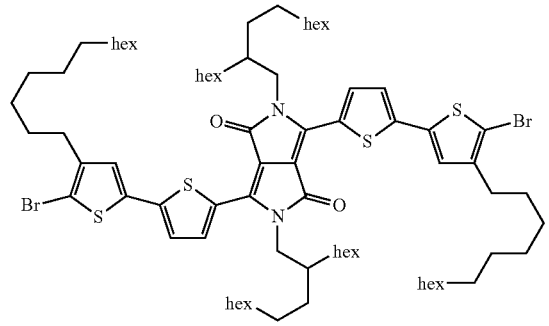

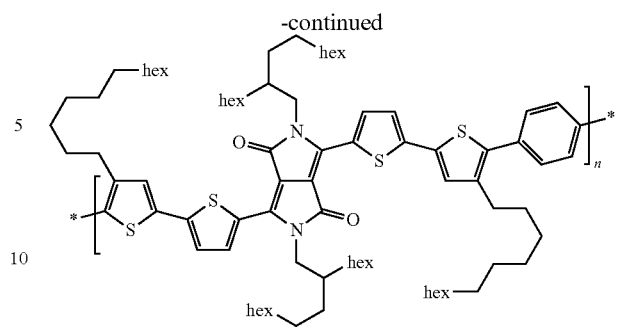

In a three neck-flask, a degassed solution of 5 g of 7, 1.185 g of 1,4-benzenediboronic acid bis(pinacol) ester, 3.773 g of $K_3PO_4$, 88.5 mg of sPhos (2-dicyclohexylphosphino-2',6'-dimethoxyphenybiphenyl) and 80.6 mg of palladium acetate in 60 ml of toluene, 20 nil of dioxane and 10 ml of water are heated to 90° C. and stirred vigorously overnight. An excess of bromobenzene is then added and after 2 hours at the same temperature an excess of phenylboronic acid pinacol ester is then added to end cap the polymer. After 2 hours to complete the end-capping, 100 mL of NaCN (1% by weight) in water is added and the mixture is stirred at 90° C. for 3 hours. The organic phase is extracted and precipitated in methanol. The residue is redissolved in tolueneand resubmitted to NaCN treatment and the organic phase is precipitated in methanol. The residue is purified by soxhlet extraction using acetone and $Et_2O$ and the polymer is then extracted with $CHCl_3$ to give 2.5 g of purple fibres.

$M_w$=27000
Pd content=30 ppm
Solubility=1% by weight in $CHCl_3$
Photophysical Properties:

UV of spin coated film on glass substrate is made from a hot chlorobenzene solution and annealed at different temperatures:

| Annealing Conditions | UV/Vis-absorption |
|---|---|
| Room temperature | 630 nm, 680 nm |

The band at 680 nm is attributed to the aggregation behaviour.

Example 6

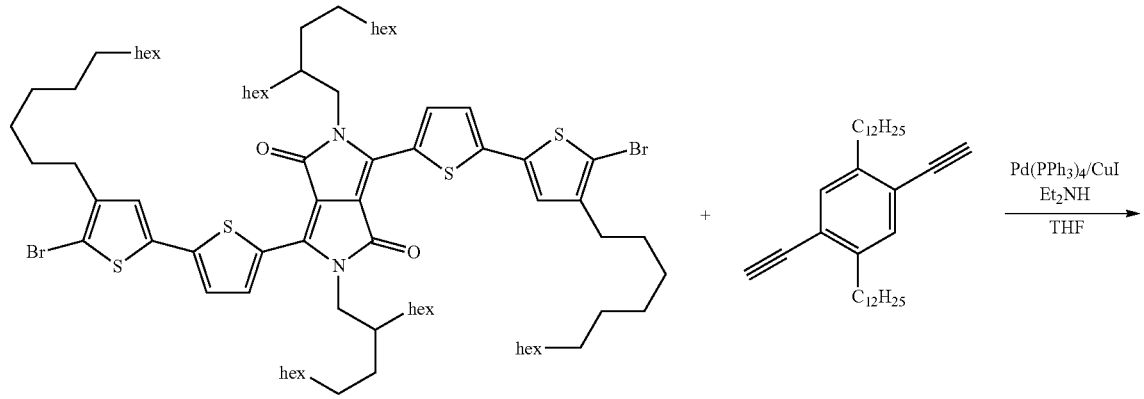

-continued

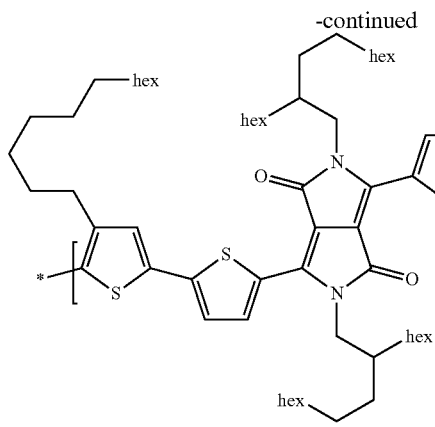

1 g of 7, 82 mg of Pd(PPh$_3$)$_4$ (10 mol %) and 13.5 mg of copper iodide (10 mol %) are dissolved in diethylamine, (0.85 ml) and THF (2 ml) in a dry, nitrogen flushed flask. The flask is then set under vacuum, flushed with nitrogen, this is repeated three times. 328 mg of the diacetylenique derivative is then added, the flask is sealed under nitrogen, heated up to 85° C. and stirred over night. The reaction mixture is dissolved in 50 ml CHCl$_3$, triturated in 500 ml MeOH, and filtrated. This action is repeated once. The solid is then purified via soxhlet extraction using MeOH, acetone and heptane and the polymer is then extracted with CHCl$_3$ to give 0.5 g of purple fibres.

M$_w$=38000

Solubility=0.5% by weight in CHCl$_3$

Photophysical Properties:

UV of spin coated film on glass substrate is made from a hot chlorobenzene solution and annealed at different temperatures:

| Annealing Conditions | UV/Vis-absorption |
| --- | --- |
| Room temperature | 650 nm, 700 nm |

The band at 700 nm is attributed to the aggregation behaviour.

The invention claimed is:

1. A polymer comprising repeating unit(s) of the formula (I):

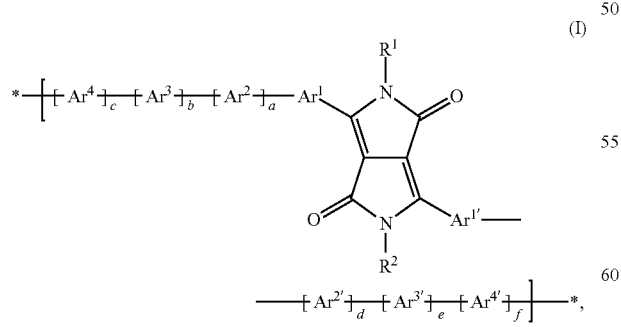

(I)

wherein a, b, c, d, e and f are 0, 1, 2, or 3;

Ar$^1$ and Ar$^{1'}$ are independently of each other a group of formula:

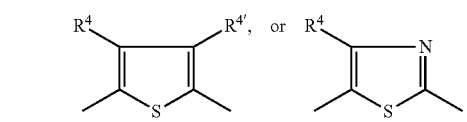

Ar$^2$, Ar$^{2'}$, Ar$^3$, Ar$^{3'}$, Ar$^4$ and Ar$^{4'}$ are independently of each other a group of formula:

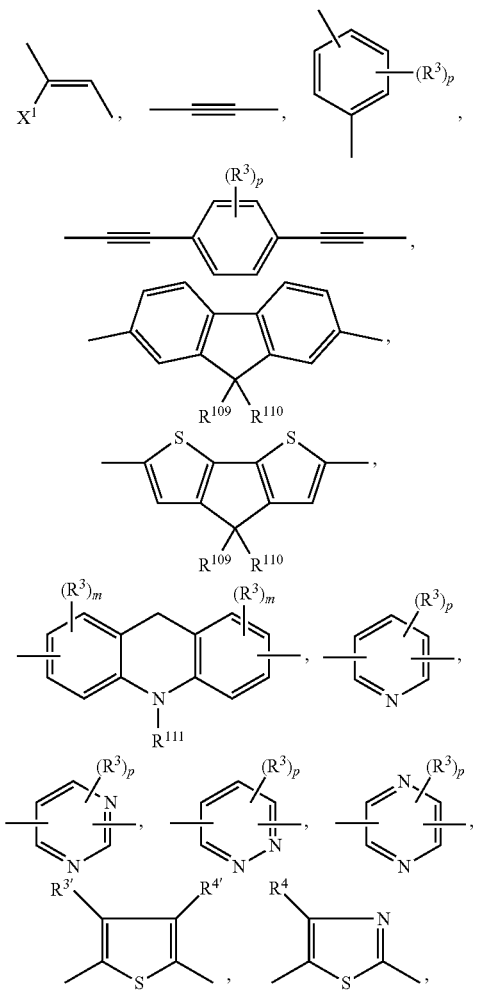

-continued

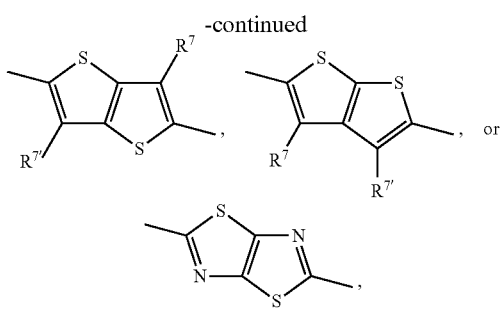

with the proviso that, if Ar2, Ar2', Ar3, Ar3', Ar4 or Ar4' are a group of formula

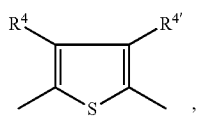

$R^4$ and $R^{4'}$ are not both hydrogen;
p is 0, 1, 2, 3 or 4;
$R^1$ and $R^2$ may be the same or different and are selected from
 hydrogen,
 a $C_1$-$C_{25}$alkyl group,
 an alkenyl group,
 an alkynyl group, which may optionally be substituted by E and/or interrupted by D,
 an allyl group, which can be substituted one to three times with $C_1$-$C_4$alkyl,
 a cycloalkyl group, which can be substituted one to three times with $C_1$-$C_8$alkyl, $C_1$-$C_8$thioalkoxy, or $C_1$-$C_8$alkoxy, or a cycloalkyl group, which can be condensed one or two times by phenyl, which can be substituted one to three times with $C_1$-$C_4$alkyl, halogen, nitro or cyano,
 a cycloalkenyl group,
 a ketone or aldehyde group,
 an ester group,
 a carbamoyl group,
 a silyl group,
 a siloxanyl group,
 $Ar^{10}$, or
 —$CR^5R^6$—$(CH_2)_g$—$Ar^{10}$; wherein
$R^5$ and $R^6$ are independently from each other
 hydrogen,
 fluorine,
 cyano, or
 $C_1$-$C_4$ alkyl, which can be substituted by fluorine, chlorine or bromine, or phenyl, which can be substituted one to three times with $C_1$-$C_4$alkyl,
$Ar^{10}$ is aryl or heteroaryl, which may optionally be substituted by G, and
g is 0, 1, 2, 3 or 4;
$R^3$ may be the same or different within one group and is selected from
 $C_1$-$C_{25}$alkyl, which may optionally be substituted by E and/or interrupted by D,
 $C_6$-$C_{24}$aryl, which may optionally be substituted by G,
 $C_2$-$C_{20}$heteroaryl, which may optionally be substituted by G,
 $C_1$-$C_{18}$alkoxy, which may optionally be substituted by E and/or interrupted by D,
 $C_7$-$C_{25}$aralkyl, wherein aryl of the aralkyl may optionally be substituted by G, or
 —CO—$R^{28}$, or
 two or more groups $R^3$ which are in the neighborhood to each other, form a ring;
$R^4$, $R^{4'}$, $R^7$ and $R^{7'}$ are independently from each other
 hydrogen,
 $C_1$-$C_{25}$alkyl, which may optionally be substituted by E and/or interrupted by D,
 $C_6$-$C_{24}$aryl, which may optionally be substituted by G,
 $C_2$-$C_{20}$heteroaryl, which may optionally be substituted by G,
 $C_1$-$C_{18}$alkoxy, which may optionally be substituted by E and/or interrupted by D,
 $C_7$-$C_{25}$aralkyl, wherein aryl of the aralkyl may optionally be substituted by G, or
 —CO—$R^{28}$; or
$R^4$ and $R^{4'}$ form a ring;
D is —CO—, —COO—, —S—, —SO—, —$SO_2$—, —O—, —$NR^{25}$—, —$CR^{23}$=$CR^{24}$—, or —C≡C—;
E is —$OR^{29}$, —$SR^{29}$, —$NR^{25}R^{26}$, —$COR^{28}$, —$COOR^{27}$, —$CNR^{25}R^{26}$, —CN, or halogen;
G is
 E,
 $C_1$-$C_{18}$alkyl, which may be interrupted by D, or
 $C_1$-$C_{18}$alkoxy which is substituted by E and/or interrupted by D; wherein
$R^{23}$, $R^{24}$, $R^{25}$ and $R^{26}$ are independently of each other
 hydrogen,
 $C_6$-$C_{18}$aryl,
 $C_6$-$C_{18}$aryl which is substituted by $C_1$-$C_{18}$alkyl, or $C_1$-$C_{18}$alkoxy,
 $C_1$-$C_{18}$alkyl, or
 $C_1$-$C_{18}$alkyl which is interrupted by an oxygen atom;
$R^{27}$ and $R^{28}$ are independently of each other
 hydrogen,
 $C_6$-$C_{18}$aryl,
 $C_6$-$C_{18}$aryl which is substituted by $C_1$-$C_{18}$alkyl, or $C_1$-$C_{18}$alkoxy,
 $C_1$-$C_{18}$alkyl, or
 $C_1$-$C_{18}$alkyl which is interrupted by an oxygen atom;
$R^{29}$ is
 hydrogen,
 $C_6$-$C_{18}$aryl,
 $C_6$-$C_{18}$aryl, which is substituted by $C_1$-$C_{18}$alkyl, or $C_1$-$C_{18}$alkoxy,
 $C_1$-$C_{18}$alkyl, or
 $C_1$-$C_{18}$alkyl which is interrupted by an oxygen atom;
$R^{109}$ and $R^{110}$ are independently of each other
 hydrogen,
 $C_1$-$C_{18}$alkyl,
 $C_1$-$C_{18}$alkyl which is substituted by E and/or interrupted by D,
 $C_6$-$C_{24}$aryl,
 $C_6$-$C_{24}$aryl which is substituted by G,
 $C_2$-$C_{20}$heteroaryl,
 $C_2$-$C_{20}$heteroaryl which is substituted by G,
 $C_2$-$C_{18}$alkenyl,
 $C_2$-$C_{18}$alkynyl,
 $C_1$-$C_{18}$alkoxy,
 $C_1$-$C_{18}$alkoxy which is substituted by E and/or interrupted by D, or
 $C_7$-$C_{25}$aralkyl; or
$R^{109}$ and $R^{110}$ together form a group of formula =$CR^{100}R^{101}$; wherein $R^{100}$ and $R^{101}$ are independently of each other
hydrogen,
$C_1$-$C_{18}$alkyl,
$C_1$-$C_{18}$alkyl which is substituted by E and/or interrupted by D,
$C_6$-$C_{24}$aryl,
$C_6$-$C_{24}$aryl which is substituted by G,
$C_2$-$C_{20}$heteroaryl; or $C_2$-$C_{20}$heteroaryl which is substituted by G; or
$R^{109}$ and $R^{110}$ together form a five or six membered ring, which is optionally substituted by
$C_1$-$C_{18}$alkyl,
$C_1$-$C_{18}$alkyl which is substituted by E and/or interrupted by D,
$C_6$-$C_{24}$aryl,
$C_6$-$C_{24}$aryl which is substituted by G,
$C_2$-$C_{20}$heteroaryl,
$C_2$-$C_{20}$heteroaryl which is substituted by G,
$C_2$-$C_{18}$alkenyl,
$C_2$-$C_{18}$alkynyl,
$C_1$-$C_{18}$alkoxy,
$C_1$-$C_{18}$alkoxy which is substituted by E and/or interrupted by D,
$C_7$-$C_{25}$aralkyl, or
—C(=O)—$R^{18}$;
$R^{111}$ is
hydrogen,
a $C_1$-$C_{25}$alkyl group,
a $C_4$-$C_{18}$cycloalkyl group,
a $C_1$-$C_{25}$alkoxy group, in which one or more carbon atoms which are not in neighborhood to each other could be replaced by —O—, —S—, or —C(=O)—O—, and/or wherein one or more hydrogen atoms can be replaced by F,
a $C_6$-$C_{24}$aryl group, or
a $C_6$-$C_{24}$aryloxy group, wherein one or more carbon atoms can be replaced by O, S, or N, and/or which can be substituted by one or more non-aromatic groups $R^{111}$;
m can be the same or different at each occurrence and is 0, 1, 2, or 3;
$X^1$ is a hydrogen atom, or a cyano group
with the proviso that, if $Ar^1$ and $Ar^{1'}$ are a group of formula

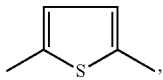

a and d are not 0.

2. The polymer according to claim 1, wherein
$R^1$ and $R^2$ are independently from each other
hydrogen;
$C_1$-$C_{25}$alkyl, which can optionally be interrupted by one or more oxygen atoms;
$C_5$-$C_{12}$cycloalkyl, which can be substituted one to three times with $C_1$-$C_8$alkyl and/or $C_1$-$C_8$alkoxy; or $C_5$-$C_{12}$cycloalkyl, which can be condensed one or two times by phenyl, which can be substituted one to three times with $C_1$-$C_4$alkyl, halogen, nitro or cyano; phenyl or 1- or 2-naphthyl which can be substituted one to three times with $C_1$-$C_8$alkyl and/or $C_1$-$C_8$alkoxy, or
—$CR^5R^6$—$(CH_2)_g$—$Ar^{10}$ wherein $R^5$ and $R^6$ are each hydrogen, $Ar^{10}$ is phenyl or 1- or 2-naphthyl, which can be substituted one to three times with $C_1$-$C_8$alkyl and/or $C_1$-$C_8$alkoxy, and g is 0 or 1.

3. The polymer according to claim 1, wherein the polymer is a co-polymer comprising repeating units of formula:

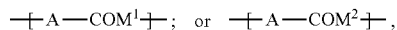

wherein
A is a repeating unit of formula I,
—$COM^1$- is selected from repeating units of formula:

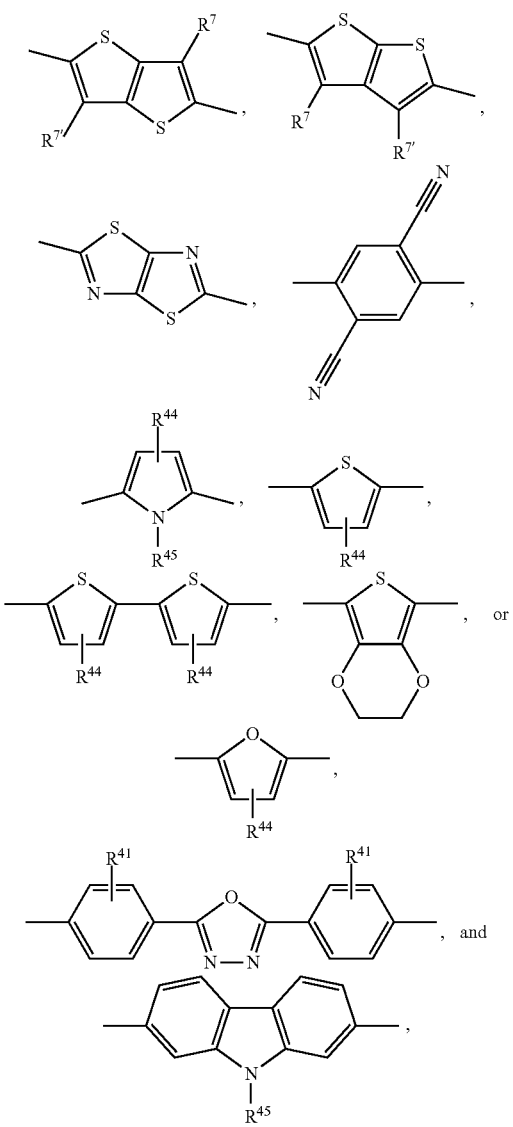

wherein
$R^7$ and $R^{7'}$ are as defined in formula I,
$R^{44}$ and $R^{41}$ are each hydrogen, $C_1$-$C_{18}$alkyl, or $C_1$-$C_{18}$alkoxy, and
$R^{45}$ is hydrogen, $C_1$-$C_{18}$alkyl, or $C_1$-$C_{18}$alkyl which is substituted by E and/or interrupted by D, wherein D and E are as defined in formula I, and —COM²— is a group of formula:

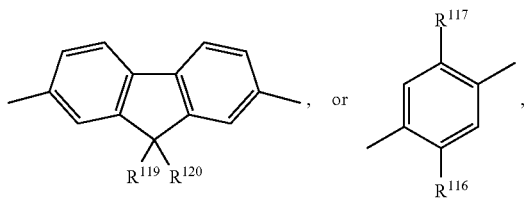

wherein
$R^{116}$ and $R^{117}$ are independently of each other hydrogen, $C_1$-$C_{18}$alkyl, which can optionally be interrupted by an oxygen atom, or $C_1$-$C_{18}$alkoxy, which can optionally be interrupted by an oxygen atom,
$R^{119}$ and $R^{120}$ are independently of each other hydrogen, $C_1$-$C_{18}$alkyl, which can optionally be interrupted by an oxygen atom, or
$R^{119}$ and $R^{120}$ together form a group of formula $=CR^{100}R^{101}$, wherein
$R^{100}$ and $R^{101}$ are independently of each other hydrogen, $C_1$-$C_{18}$alkyl, or
$R^{119}$ and $R^{120}$ together form a five or six membered ring, which optionally can be substituted by $C_1$-$C_{18}$alkyl.

4. The polymer according to claim 3, wherein the polymer is a co-polymer of formula:

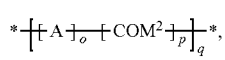 (ACOM2)

and optionally,

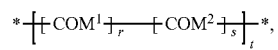 (COM12)

wherein
the order of the unit

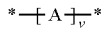

and the unit

is arbitrary in the repeating unit (ACOM2), and the order of the unit

and the unit

is arbitrary in the repeating unit (COM12),
is 1,
p is 0 or 1,
r is 0 or 1,
s is 0 or 1,
a molar amount of the repeating unit (ACOM2) is from 0.005 to 1 and a molar amount of the repeating unit (COM12) is from 0.995 to 0, with respect to a total of repeating units included in the polymer.

5. The polymer according to claim 1, wherein $Ar^1$ and $Ar^{1'}$ are the same and are a group of formula:

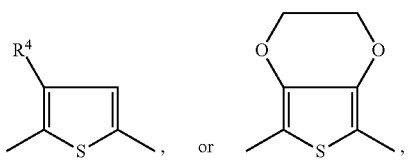

and
$Ar^2$, $Ar^{2'}$, $Ar^3$, $Ar^{3'}$, $Ar^4$ and $Ar^{4'}$ are independently of each other a group of formula:

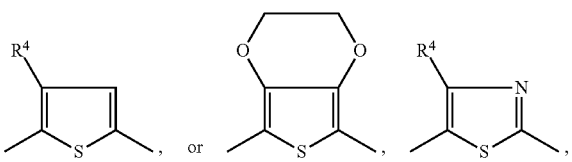

wherein
p stands for 0, 1, or 2,
$R^3$ may be the same or different within one group and is selected from $C_1$-$C_{25}$alkyl, which may optionally be substituted by E and/or interrupted by D, or $C_1$-$C_{18}$alkoxy, which may optionally be substituted by E and/or interrupted by D,
$R^4$ is $C_6$-$C_{25}$alkyl, which may optionally be substituted by E and/or interrupted by D, $C_6$-$C_{14}$aryl, which may optionally be substituted by G, $C_1$-$C_{25}$alkoxy, which may optionally be substituted by E and/or interrupted by D, or $C_7$-$C_{15}$aralkyl, wherein aryl of the aralkyl may optionally be substituted by G,
D is —CO—, —COO—, —S—, —SO—, —SO₂—, —O—, —NR²⁵—, wherein $R^{25}$ is $C_1$-$C_{12}$alkyl,
E is —OR²⁹; —SR²⁹; —NR²⁵R²⁵; —COR²⁸; —COOR²⁷; —CONR²⁵R²⁵; or —CN, and
G is —OR²⁹; —SR²⁹; —NR²⁵R²⁵; —COR²⁸; —COOR²⁷; —CONR²⁵R²⁵; —CN, or $C_1$-$C_{18}$alkyl,
wherein
$R^{25}$, $R^{27}$, $R^{28}$ and $R^{29}$ are independently of each other $C_1$-$C_{12}$alkyl.

6. The polymer according to claim 1 wherein

 and
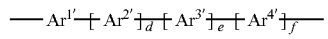

may be the same or different, and are a group of formula:

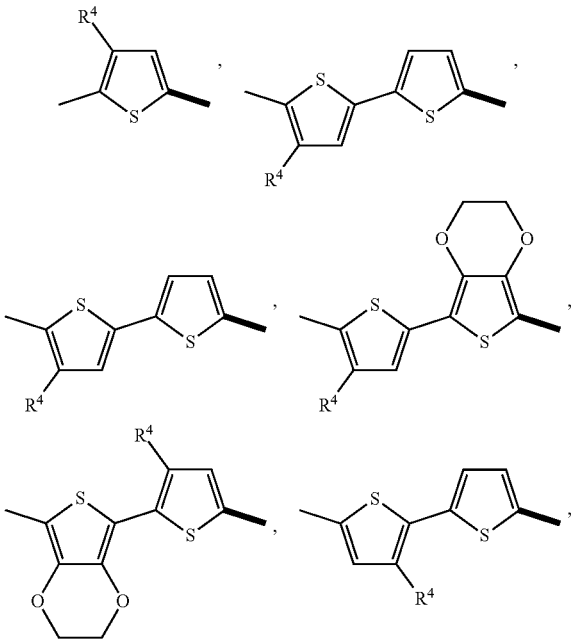

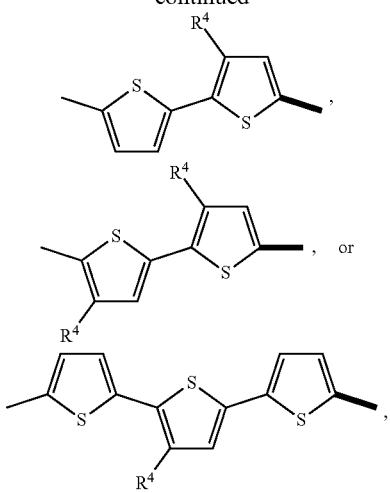

wherein

■ indicates the bond to the diketopyrrolopyrrole skeleton, $R^4$ and $R^{4'}$ are each $C_6$-$C_{25}$alkyl, which may optionally be substituted by E and/or interrupted by D, $C_6$-$C_{14}$aryl, which may optionally be substituted by G, $C_1$-$C_{25}$alkoxy, which may optionally be substituted by E and/or interrupted by D, or $C_7$-$C_{15}$aralkyl, wherein aryl of the aralkyl may optionally be substituted by G, D is —CO—, —COO—, —S—, —SO—, —SO$_2$—, —O—, —NR$^{25}$—, wherein $R^{25}$ is $C_1$-$C_{12}$alkyl, E is —OR$^{29}$; —SR$^{29}$; —NR$^{25}$R$^{25}$; —COR$^{28}$; —COOR$^{27}$; —CONR$^{25}$R$^{25}$; or —CN, and G is —OR$^{29}$; —SR$^{29}$; —NR$^{25}$R$^{25}$; —COR$^{28}$; —COOR$^{27}$; —CONR$^{25}$R$^{25}$; —CN, or $C_1$-$C_{18}$alkyl, wherein $R^{25}$, $R^{27}$, $R^{28}$ and $R^{29}$ are independently of each other $C_1$-$C_{12}$alkyl.

7. The polymer according to claim 1, wherein the polymer comprises repeating units of the formula:

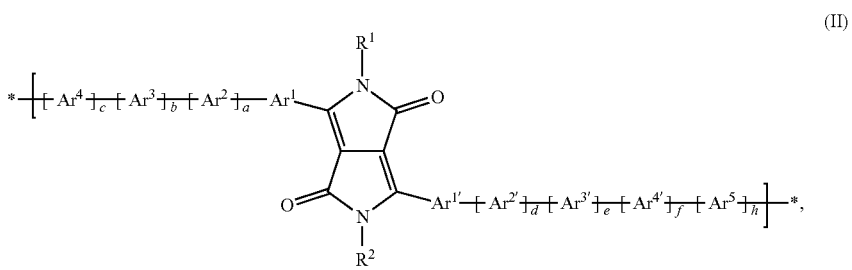

(II)

wherein a, b, c, d, e, f, $R^1$, $R^2$, $Ar^1$, $Ar^{1'}$, $Ar^2$, $Ar^{2'}$, $Ar^3$, $Ar^{3'}$, $Ar^4$ and $Ar^{4'}$ are as defined in formula I, h is 1, and $Ar^5$ is a group of formula:

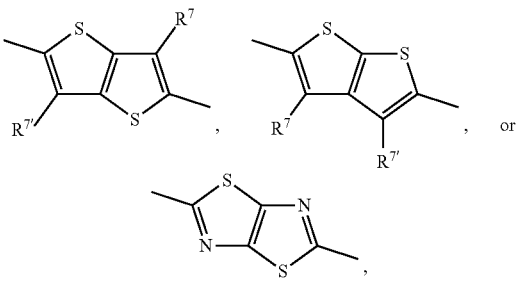

wherein $R^7$ and $R^{7'}$ are as defined in formula I.

8. The polymer according to claim 1, comprising repeating units of the formula:

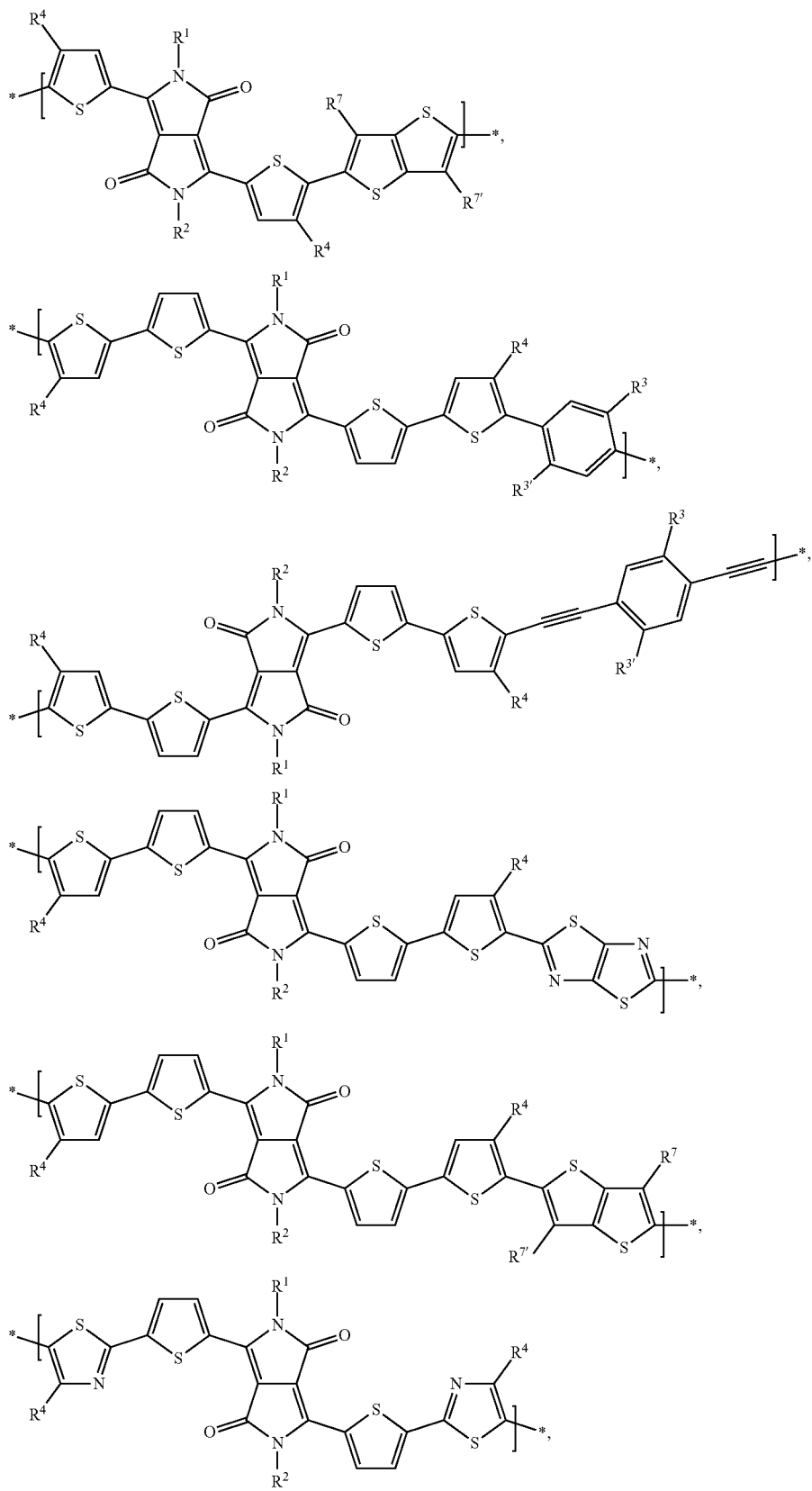

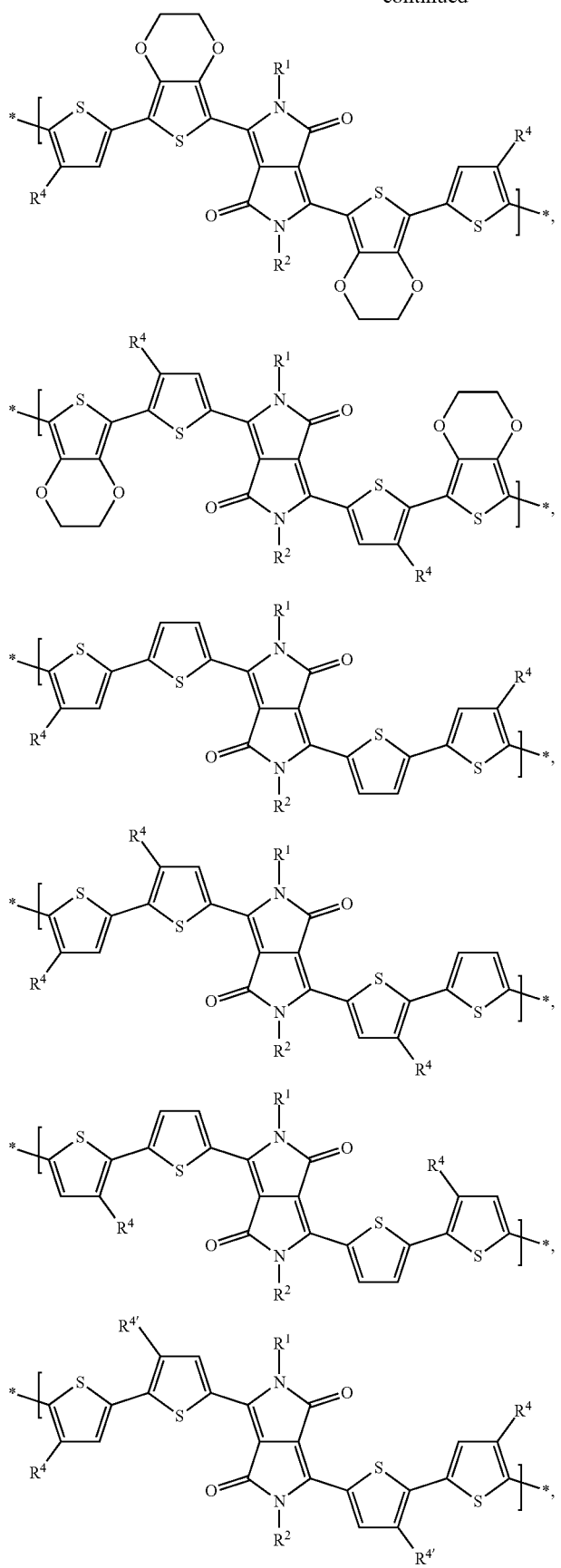

-continued

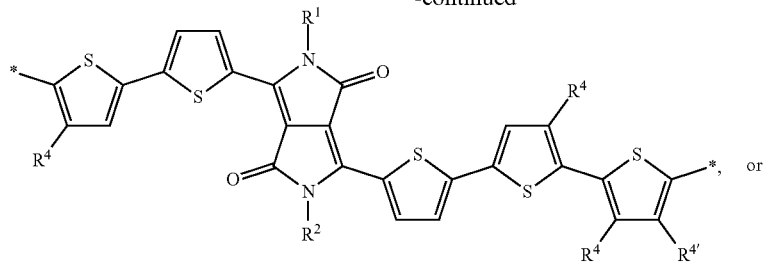

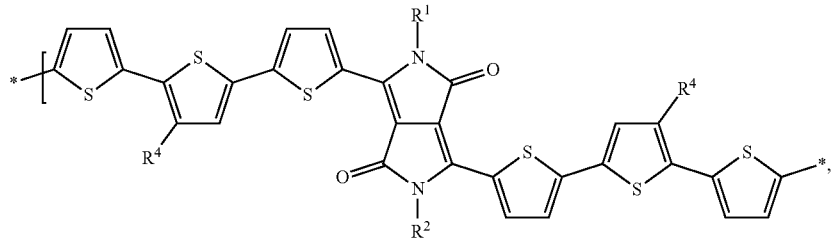

wherein $R^1$ and $R^2$ are independently from each other $C_1$-$C_{25}$alkyl, $R^3$ and $R^{3'}$ are independently from each other $C_6$-$C_{25}$alkyl, which may optionally be interrupted by one or more oxygen atoms, $R^4$ and $R^{4'}$ are independently from each other $C_6$-$C_{25}$alkyl, which may optionally be interrupted by one or more oxygen atoms, and $R^7$ and $R^{7'}$ are independently from each other $C_6$-$C_{25}$alkyl, which may optionally be interrupted by one or more oxygen atoms.

9. A semiconductor device, comprising the polymer according to claim 1.

10. The semiconductor device according to claim 9, which is a solar cell, comprising in this order:
    (a) a cathode,
    (b) optionally a transition layer,
    (c) a photoactive layer,
    (d) optionally a smoothing layer,
    (e) an anode,
    (f) a substrate, wherein the photoactive layer comprises the polymer.

11. The semiconductor device according to claim 1, which is a thin film transistor device comprising:
    a plurality of electrically conducting gate electrodes disposed on a substrate;
    a gate insulator layer disposed on the electrically conducting gate electrodes;
    a plurality of sets of electrically conductive source and drain electrodes disposed on the gate insulator layer such that each of the sets is in alignment with each of the gate electrodes;
    an organic semiconductor layer disposed in the channel between source and drain electrodes on the gate insulator layer substantially overlapping the gate electrodes; wherein the organic semiconductor layer comprises the polymer, or a mixture containing the polymer.

12. A process for the preparation of an organic semiconductor device according to claim 9, the process comprising applying a solution and/or dispersion of the polymer in an organic solvent to a substrate and removing the solvent.

13. A monomer of the formula (X):

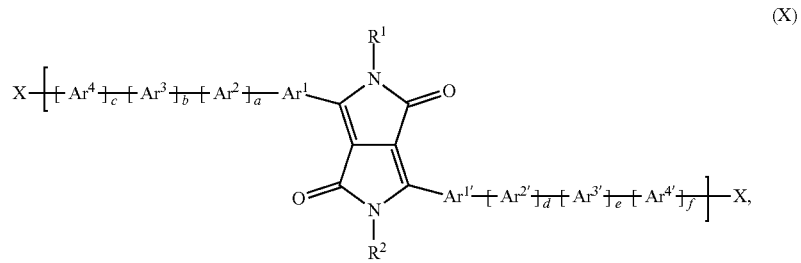

(X)

wherein a, b, c, d, e and f are 0, 1, 2, or 3;

$Ar^1$ and $Ar^{1'}$ are independently of each other a group of formula:

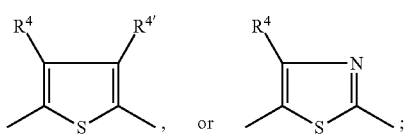

$Ar^2$, $Ar^{2'}$, $Ar^3$, $Ar^{3'}$, $Ar^4$ and $Ar^{4'}$ are independently of each other a group of formula:

[Structures shown: various substituent groups including alkenyl with X¹, alkynyl, phenyl with (R³)ₚ, diethynyl phenyl with (R³)ₚ, fluorene with R¹⁰⁹/R¹¹⁰, dithienocyclopentadiene with R¹⁰⁹/R¹¹⁰, carbazole with (R³)ₘ and R¹¹¹, pyridine with (R³)ₚ, pyridazine/pyrimidine/pyrazine with (R³)ₚ, thiophenes with R⁴/R⁴′, thiazole with R⁴, dithienothiophenes with R⁷/R⁷′, and thiazolothiazole]

with the proviso that, if Ar2, Ar2', Ar3, Ar3', Ar4 or Ar4' are a group of formula

[Structure: thiophene with R⁴ and R⁴′ substituents]

$R^4$ and $R^{4'}$ are not both hydrogen;
p is 0, 1, 2, 3 or 4;
$R^1$ and $R^2$ may be the same or different and are selected from
  hydrogen,
  a $C_1$-$C_{25}$alkyl group,
  an alkenyl group,
  an alkynyl group, which may optionally be substituted by E and/or interrupted by D,
  an allyl group, which can be substituted one to three times with $C_1$-$C_4$alkyl,
  a cycloalkyl group, which can be substituted one to three times with $C_1$-$C_8$alkyl, $C_1$-$C_8$thioalkoxy, or $C_1$-$C_8$alkoxy, or a cycloalkyl group, which can be condensed one or two times by phenyl, which can be substituted one to three times with $C_1$-$C_4$alkyl, halogen,
  nitro or cyano,
  a cycloalkenyl group,
  a ketone or aldehyde group,
  an ester group,
  a carbamoyl group,
  a silyl group,
  a siloxanyl group,
  $Ar^{10}$, or
  $-CR^5R^6-(CH_2)_g-Ar^{10}$; wherein
$R^5$ and $R^6$ are independently from each other
  hydrogen,
  fluorine,
  cyano, or
  $C_1$-$C_4$ alkyl, which can be substituted by fluorine, chlorine or bromine, or
  phenyl, which can be substituted one to three times with $C_1$-$C_4$alkyl,
$Ar^{10}$ is aryl or heteroaryl, which may optionally be substituted by G, and
g is 0, 1, 2, 3 or 4;
$R^3$ may be the same or different within one group and is selected from
  $C_1$-$C_{25}$alkyl, which may optionally be substituted by E and/or interrupted by D,
  $C_6$-$C_{24}$aryl, which may optionally be substituted by G,
  $C_2$-$C_{20}$heteroaryl, which may optionally be substituted by G,
  $C_1$-$C_{18}$alkoxy, which may optionally be substituted by E and/or interrupted by D,
  $C_7$-$C_{25}$aralkyl, wherein aryl of the aralkyl may optionally be substituted by G, or
  $-CO-R^{28}$, or
  two or more groups $R^3$ which are in the neighborhood to each other, form a ring;
$R^4$, $R^{4'}$, $R^7$ and $R^{7'}$ are independently from each other
  hydrogen,
  $C_1$-$C_{25}$alkyl, which may optionally be substituted by E and/or interrupted by D,
  $C_6$-$C_{24}$aryl, which may optionally be substituted by G,
  $C_2$-$C_{20}$heteroaryl, which may optionally be substituted by G,
  $C_1$-$C_{18}$alkoxy, which may optionally be substituted by E and/or interrupted by D,
  $C_7$-$C_{25}$aralkyl, wherein aryl of the aralkyl may optionally be substituted by G, or
  $-CO-R^{28}$; or
$R^4$ and $R^{4'}$ form a ring;
D is $-CO-$, $-COO-$, $-S-$, $-SO-$, $-SO_2-$, $-O-$, $-NR^{25}-$, $-CR^{23}=CR^{24}-$, or $-C\equiv C-$;
E is $-OR^{29}$, $-SR^{29}$, $-NR^{25}R^{26}$, $-COR^{28}$, $-COOR^{27}$, $-CNR^{25}R^{26}$, $-CN$, or halogen;
G is
  E,
  $C_1$-$C_{18}$alkyl, which may be interrupted by D, or
  $C_1$-$C_{18}$alkoxy which is substituted by E and/or interrupted by D; wherein $R^{23}$, $R^{24}$, $R^{25}$ and $R^{26}$ are independently of each other
hydrogen,
$C_6$-$C_{18}$aryl,
$C_6$-$C_{18}$aryl which is substituted by $C_1$-$C_{18}$alkyl, or $C_1$-$C_{18}$alkoxy,
$C_1$-$C_{18}$alkyl, or
$C_1$-$C_{18}$alkyl which is interrupted by an oxygen atom;
$R^{27}$ and $R^{28}$ are independently of each other
hydrogen,
$C_6$-$C_{18}$aryl,
$C_6$-$C_{18}$aryl which is substituted by $C_1$-$C_{18}$alkyl, or $C_1$-$C_{18}$alkoxy,
$C_1$-$C_{18}$alkyl, or
$C_1$-$C_{18}$alkyl which is interrupted by an oxygen atom;
$R^{29}$ is
hydrogen,
$C_6$-$C_{18}$aryl,
$C_6$-$C_{18}$aryl, which is substituted by $C_1$-$C_{18}$alkyl, or $C_1$-$C_{18}$alkoxy,
$C_1$-$C_{18}$alkyl, or
$C_1$-$C_{18}$alkyl which is interrupted by an oxygen atom;
$R^{109}$ and $R^{110}$ are independently of each other
hydrogen,
$C_1$-$C_{18}$alkyl,
$C_1$-$C_{18}$alkyl which is substituted by E and/or interrupted by D,
$C_6$-$C_{24}$aryl,
$C_6$-$C_{24}$aryl which is substituted by G,
$C_2$-$C_{20}$heteroaryl,
$C_2$-$C_{20}$heteroaryl which is substituted by G,
$C_2$-$C_{18}$alkenyl,
$C_2$-$C_{18}$alkynyl,
$C_1$-$C_{18}$alkoxy,
$C_1$-$C_{18}$alkoxy which is substituted by E and/or interrupted by D, or
$C_7$-$C_{25}$aralkyl; or
$R^{109}$ and $R^{110}$ together form a group of formula $=CR^{100}R^{101}$; wherein
$R^{100}$ and $R^{101}$ are independently of each other
hydrogen,
$C_1$-$C_{18}$alkyl,
$C_1$-$C_{18}$alkyl which is substituted by E and/or interrupted by D,
$C_6$-$C_{24}$aryl,
$C_6$-$C_{24}$aryl which is substituted by G,
$C_2$-$C_{20}$heteroaryl; or $C_2$-$C_{20}$heteroaryl which is substituted by G; or
$R^{109}$ and $R^{110}$ together form a five or six membered ring, which is optionally substituted by
$C_1$-$C_{18}$alkyl,
$C_1$-$C_{18}$alkyl which is substituted by E and/or interrupted by D,
$C_6$-$C_{24}$aryl,
$C_6$-$C_{24}$aryl which is substituted by G,
$C_2$-$C_{20}$heteroaryl,
$C_2$-$C_{20}$heteroaryl which is substituted by G,
$C_2$-$C_{18}$alkenyl,
$C_2$-$C_{18}$alkynyl,
$C_1$-$C_{18}$alkoxy,
$C_1$-$C_{18}$alkoxy which is substituted by E and/or interrupted by D,
$C_7$-$C_{25}$aralkyl, or
—C(O)—$R^{18}$;
$R^{111}$ is
hydrogen,
a $C_1$-$C_{25}$alkyl group,
a $C_4$-$C_{18}$cycloalkyl group,
a $C_1$-$C_{25}$alkoxy group, in which one or more carbon atoms which are not in neighborhood to each other could be replaced by —O—, —S—, or —C(=O)—O—, and/or wherein one or more hydrogen atoms can be replaced by F,
a $C_6$-$C_{24}$aryl group, or
a $C_6$-$C_{24}$aryloxy group, wherein one or more carbon atoms can be replaced by O, S, or N, and/or which can be substituted by one or more non-aromatic groups $R^{111}$;
m can be the same or different at each occurrence and is 0, 1, 2, or 3;
$X^1$ is a hydrogen atom, or a cyano group
with the proviso that, if $Ar^1$ and $Ar^{1'}$ are a group of formula

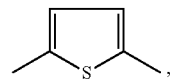, a and d are not 0; and
X is
$ZnX^{12}$, wherein $X^{12}$ is a halogen atom;
—$SnR^{207}R^{208}R^{209}$, wherein $R^{207}$, $R^{208}$ and $R^{209}$ are identical or different and are hydrogen or $C_1$-$C_6$alkyl, wherein two radicals among $R^{207}$, $R^{208}$ and $R^{209}$ optionally form a common ring and $R^{207}$, $R^{208}$ and $R^{209}$ are optionally branched or unbranched; or
$OS(O)_2CF_3$, —$OS(O)_2$-aryl, —$OS(O)_2CH_3$, —$B(OH)_2$, —$B(OY^1)_2$,

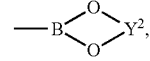

—$BF_4Na$, or —$BF_4K$, wherein $Y^1$ is independently in each occurrence a $C_1$-$C_{10}$alkyl group and $Y^2$ is independently in each occurrence —$CY^3Y^4$—$CY^5Y^6$— or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen or a $C_1$-$C_{10}$alkyl group.

14. A process for preparing the polymer according to claim 3, the process comprising reacting a dibromide of formula Br-A-Br with an equimolar amount of a diboronic acid or diboronate of formula:

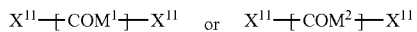

under the catalytic action of Pd and triphenylphosphine, wherein
$X^{11}$ is independently in each occurrence —$B(OH)_2$, —$B(OY^1)_2$ or

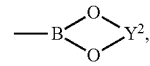

wherein $Y^1$ is independently in each occurrence a $C_1$-$C_{10}$alkyl group and $Y^2$ is independently in each occurrence —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen or a $C_1$-$C_{10}$alkyl group.

* * * * *